(12) United States Patent
Grinvald et al.

(10) Patent No.: US 7,912,534 B2
(45) Date of Patent: Mar. 22, 2011

(54) CHARACTERIZATION OF MOVING OBJECTS IN A STATIONARY BACKGROUND

(75) Inventors: Amiram Grinvald, Rehovot (IL); Darin Nelson, Rehovot (IL); Ivo Vanzetta, Marseilles (FR)

(73) Assignee: Yeda Research and Development Co. Ltd., Rehovot (IL)

( * ) Notice: Subject to any disclaimer, the term of this patent is extended or adjusted under 35 U.S.C. 154(b) by 668 days.

(21) Appl. No.: 10/954,014

(22) Filed: Sep. 29, 2004

(65) Prior Publication Data

US 2005/0131284 A1  Jun. 16, 2005

Related U.S. Application Data

(63) Continuation of application No. PCT/IL03/00275, filed on Apr. 2, 2003.

(60) Provisional application No. 60/369,658, filed on Apr. 2, 2002.

(51) Int. Cl.
*A61B 5/00* (2006.01)

(52) U.S. Cl. .......... 600/476; 600/323; 600/478; 356/40

(58) Field of Classification Search .............. 600/407, 600/476, 478, 323; 356/39–40; 382/128
See application file for complete search history.

(56) References Cited

U.S. PATENT DOCUMENTS

| | | | | |
|---|---|---|---|---|
| 4,998,533 | A * | 3/1991 | Winkelman | 600/368 |
| 5,217,456 | A * | 6/1993 | Narciso, Jr. | 606/15 |
| 5,279,298 | A | 1/1994 | Flower | |
| 5,297,554 | A * | 3/1994 | Glynn et al. | 600/476 |
| 5,348,003 | A * | 9/1994 | Caro | 600/310 |
| 5,463,426 | A | 10/1995 | Grinvald et al. | |
| 5,515,847 | A * | 5/1996 | Braig et al. | 600/316 |
| 5,572,996 | A * | 11/1996 | Doiron et al. | 600/317 |
| 5,598,842 | A * | 2/1997 | Ishihara et al. | 600/322 |
| 5,666,956 | A * | 9/1997 | Buchert | 600/473 |
| 5,706,821 | A * | 1/1998 | Matcher et al. | 600/310 |
| 5,722,398 | A * | 3/1998 | Ishihara et al. | 600/322 |
| 5,741,213 | A * | 4/1998 | Kouchi et al. | 600/310 |
| 5,769,076 | A * | 6/1998 | Maekawa et al. | 600/322 |

(Continued)

FOREIGN PATENT DOCUMENTS

WO   WO-99/63882 A1   12/1999

(Continued)

OTHER PUBLICATIONS

Yoshinobu Sato, et al., "Automatic Extraction and Measurement of Leukocyte Motion in Microvessels Using Spatiotemporal Image Analysis", Engineering, Apr. 1997, vol. 44, No. 4, pp. 225-236.

(Continued)

*Primary Examiner* — Brian Casler
*Assistant Examiner* — Jonathan G Cwern
(74) *Attorney, Agent, or Firm* — Fish & Richardson P.C.

(57) ABSTRACT

A method and system for determination and mapping the quantity of chromophores having a distinct spectrum attached to moving objects in an spectrally rich environment that may include multiple chromophores attached to stationary objects. Au area of interest is imaged at different times and different wavelengths, and the spectral properties of the chromophores attached to the moving objects are separated from the stationary spectral properties of the background, followed by spectral analysis of the moving objects to determine their quantity. Application to the retinal vasculature is illustrated, showing the imaging, analyzing and quantifying of the oxygen saturation of retinal blood, resolved for the different vascular compartments, including capillaries, arterioles, venules, arteries, and veins.

18 Claims, 11 Drawing Sheets

U.S. PATENT DOCUMENTS

| | | | | |
|---|---|---|---|---|
| 5,784,162 | A * | 7/1998 | Cabib et al. | 356/456 |
| 5,787,185 | A * | 7/1998 | Clayden | 382/115 |
| 5,791,345 | A * | 8/1998 | Ishihara et al. | 600/368 |
| 5,811,814 | A | 9/1998 | Leone et al. | |
| 5,931,779 | A * | 8/1999 | Arakaki et al. | 600/310 |
| 5,934,278 | A * | 8/1999 | Ishihara et al. | 600/476 |
| 5,974,338 | A * | 10/1999 | Asano et al. | 600/323 |
| 5,983,120 | A * | 11/1999 | Groner et al. | 600/310 |
| 6,061,583 | A * | 5/2000 | Ishihara et al. | 600/322 |
| 6,081,612 | A * | 6/2000 | Gutkowicz-Krusin et al. | 382/128 |
| 6,088,087 | A * | 7/2000 | Graves et al. | 356/39 |
| 6,104,939 | A | 8/2000 | Groner et al. | |
| 6,208,749 | B1 * | 3/2001 | Gutkowicz-Krusin et al. | 382/128 |
| 6,350,431 | B1 * | 2/2002 | Snow et al. | 424/9.6 |
| 6,351,663 | B1 | 2/2002 | Flower et al. | |
| 6,362,175 | B1 * | 3/2002 | Vinogradov et al. | 514/185 |
| 6,512,936 | B1 * | 1/2003 | Monfre et al. | 600/322 |
| 6,512,937 | B2 * | 1/2003 | Blank et al. | 600/322 |
| 6,567,678 | B1 * | 5/2003 | Oosta et al. | 600/316 |
| 6,571,118 | B1 * | 5/2003 | Utzinger et al. | 600/476 |
| 6,577,884 | B1 | 6/2003 | Boas | |
| 6,587,701 | B1 * | 7/2003 | Stranc et al. | 600/310 |
| 6,721,582 | B2 * | 4/2004 | Trepagnier et al. | 600/316 |
| 6,782,289 | B1 | 8/2004 | Strauss | |
| 6,826,424 | B1 * | 11/2004 | Zeng et al. | 600/476 |
| 6,844,195 | B2 * | 1/2005 | Craine | 436/66 |
| 6,859,658 | B1 * | 2/2005 | Krug | 600/323 |
| 6,869,430 | B2 * | 3/2005 | Balbierz et al. | 606/41 |
| 6,889,075 | B2 * | 5/2005 | Marchitto et al. | 600/473 |
| 6,898,451 | B2 * | 5/2005 | Wuori | 600/322 |
| 6,898,458 | B2 * | 5/2005 | Zeng et al. | 600/476 |
| 6,902,935 | B2 * | 6/2005 | Kaufman et al. | 436/63 |
| 6,917,038 | B2 * | 7/2005 | Zheng et al. | 250/339.04 |
| 7,025,765 | B2 * | 4/2006 | Balbierz et al. | 606/41 |
| 7,054,674 | B2 * | 5/2006 | Cane et al. | 600/407 |
| 7,115,841 | B2 * | 10/2006 | Zeng et al. | 219/476 |
| 7,190,452 | B2 * | 3/2007 | Zeng et al. | 356/326 |
| 7,217,266 | B2 * | 5/2007 | Anderson et al. | 606/12 |
| 7,225,005 | B2 * | 5/2007 | Kaufman et al. | 600/322 |
| 7,253,894 | B2 * | 8/2007 | Zeng et al. | 356/326 |
| 2001/0056237 | A1 * | 12/2001 | Cane et al. | 600/475 |
| 2002/0007122 | A1 * | 1/2002 | Kaufman et al. | 600/476 |
| 2002/0007123 | A1 * | 1/2002 | Balas | 600/476 |
| 2002/0016533 | A1 * | 2/2002 | Marchitto et al. | 600/310 |
| 2002/0016534 | A1 * | 2/2002 | Trepagnier et al. | 600/316 |
| 2002/0026127 | A1 * | 2/2002 | Balbierz et al. | 600/567 |
| 2002/0026188 | A1 * | 2/2002 | Balbierz et al. | 606/41 |
| 2002/0076820 | A1 * | 6/2002 | Craine | 436/66 |
| 2002/0103439 | A1 * | 8/2002 | Zeng et al. | 600/476 |
| 2002/0111545 | A1 * | 8/2002 | Lindberg et al. | 600/322 |
| 2002/0127735 | A1 * | 9/2002 | Kaufman et al. | 436/172 |
| 2002/0197728 | A1 * | 12/2002 | Kaufman et al. | 436/164 |
| 2003/0032064 | A1 * | 2/2003 | Soller et al. | 435/7.1 |
| 2003/0036751 | A1 * | 2/2003 | Anderson et al. | 606/9 |
| 2003/0050541 | A1 * | 3/2003 | Wuori | 600/316 |
| 2003/0114762 | A1 * | 6/2003 | Balas et al. | 600/476 |
| 2003/0146385 | A1 * | 8/2003 | Zheng et al. | 250/339.04 |
| 2003/0163049 | A1 * | 8/2003 | Balas | 600/476 |
| 2003/0207250 | A1 * | 11/2003 | Kaufman et al. | 435/4 |
| 2004/0044287 | A1 * | 3/2004 | Lin et al. | 600/475 |
| 2004/0116814 | A1 * | 6/2004 | Stranc et al. | 600/473 |
| 2005/0054936 | A1 * | 3/2005 | Balas | 600/476 |
| 2005/0064602 | A1 * | 3/2005 | Kaufman et al. | 436/164 |
| 2005/0090751 | A1 * | 4/2005 | Balas | 600/476 |
| 2005/0131284 | A1 * | 6/2005 | Grinvald et al. | 600/323 |
| 2005/0143662 | A1 * | 6/2005 | Marchitto et al. | 600/473 |
| 2005/0167621 | A1 * | 8/2005 | Zeng et al. | 250/580 |
| 2005/0192493 | A1 * | 9/2005 | Wuori | 600/322 |
| 2005/0203421 | A1 * | 9/2005 | Zeng et al. | 600/476 |
| 2005/0203423 | A1 * | 9/2005 | Zeng et al. | 600/476 |
| 2005/0251049 | A1 * | 11/2005 | Cane et al. | 600/476 |
| 2006/0141633 | A1 * | 6/2006 | Balas | 436/164 |
| 2006/0195022 | A1 * | 8/2006 | Trepagnier et al. | 600/316 |
| 2006/0241577 | A1 * | 10/2006 | Balbierz et al. | 606/32 |
| 2007/0043341 | A1 * | 2/2007 | Anderson et al. | 606/12 |

FOREIGN PATENT DOCUMENTS

| | | |
|---|---|---|
| WO | 0006015 | 2/2000 |
| WO | WO-01/22741 A2 | 3/2001 |

OTHER PUBLICATIONS

Brian Holeman, et al., "Dynamic Scene Analysis for Vessel Structure Determination", Southeastcon 1989 Proceedings, Energy and information technologies in the southeast, Columbia, SC, USA, Apr. 9, 1989, pp. 1072-1073.

J. Domingo, et al., "Irregular motion recovery in fluorescein angiograms", Pattern Recognition Letters 1997, vol. 18, No. 1, pp. 805-821.

J. Sklenar, et al., "Parametric Imaging for Myocardial Contrast Echocardiography: Pixel-by-Pixel Incorporation of Information from Both Spatial and Temporal Domains", Computers in Cardiology, 1998, vol. 25, pp. 461-464.

Robert A. Linsenmeier, et al., "Metabolic Dependence of Photoreceptors on the Choroid in the Normal and Detached Retina", Investigative Ophthalmology & Visual Science, Sep. 2000, vol. 41, No. 10, pp. 3117-3123.

Robert A. Linsenmeier, et al., "Retinal Hypoxia in Long-Term Diabetic Cats", Investigative Ophthalmology & Visual Science, Aug. 1998, vol. 39, No. 9, pp. 1647-1657.

Kurt R. Denninghoff, M.D., et al., "Retinal Imaging Techniques in Diabetes", Diabetes Technology & Therapeutics, 2000, vol. 2, No. 1, pp. 111-113.

M. Bruce Shields, M.D., "Textbook of Glaucoma", 4th edition, Lippincott Williams and Wilkins, Philadelphia, 1997.

Taylor, Charles A. et al. "Finite element Modeling of three-dimensional pulsatile flow in the abdominal aorta: Relevance to athereosclerosis." Annals of Biomedical Engineering, vol. 26, pp. 975-987, 1998.

Taylor, Charles A. et al. "In vivo quantification of blood flow and wall shear stress in the human abdominal aorta during lower limb exercise." Annals of biomedical Engineering, vol. 39, pp. 402-408, 2002.

Wong, Tien Yin et al. "Retinal Microvascular Abnormalities and Incident Stroke: The Atherosclerosis Risk in Communities Study." Lancet 2001, 358: 1134-40.

\* cited by examiner

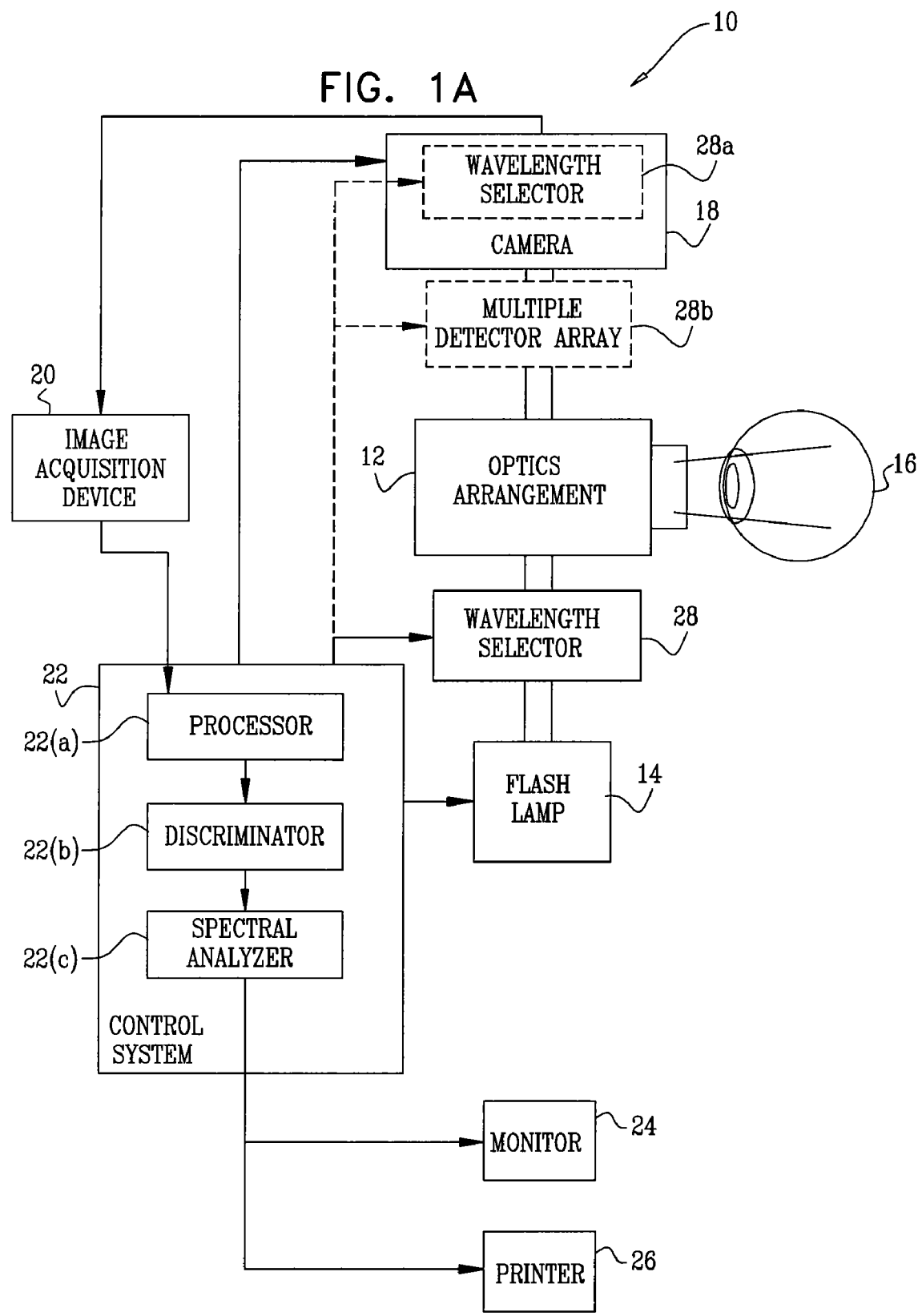

FIG. 2A
TIME=$t_A$
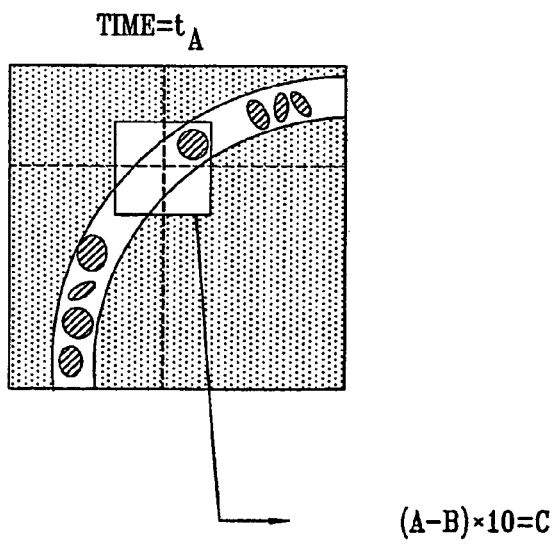
FIG. 2B
TIME=$t_B$
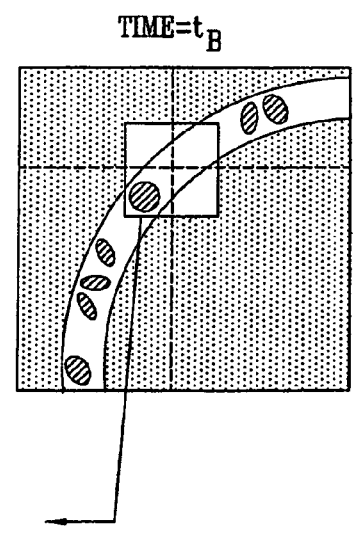
(A−B)×10=C
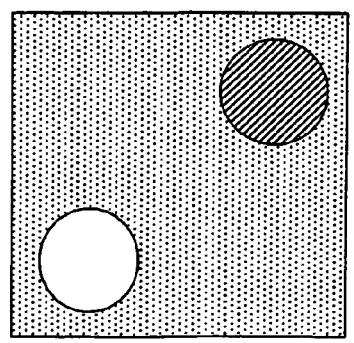
FIG. 2C

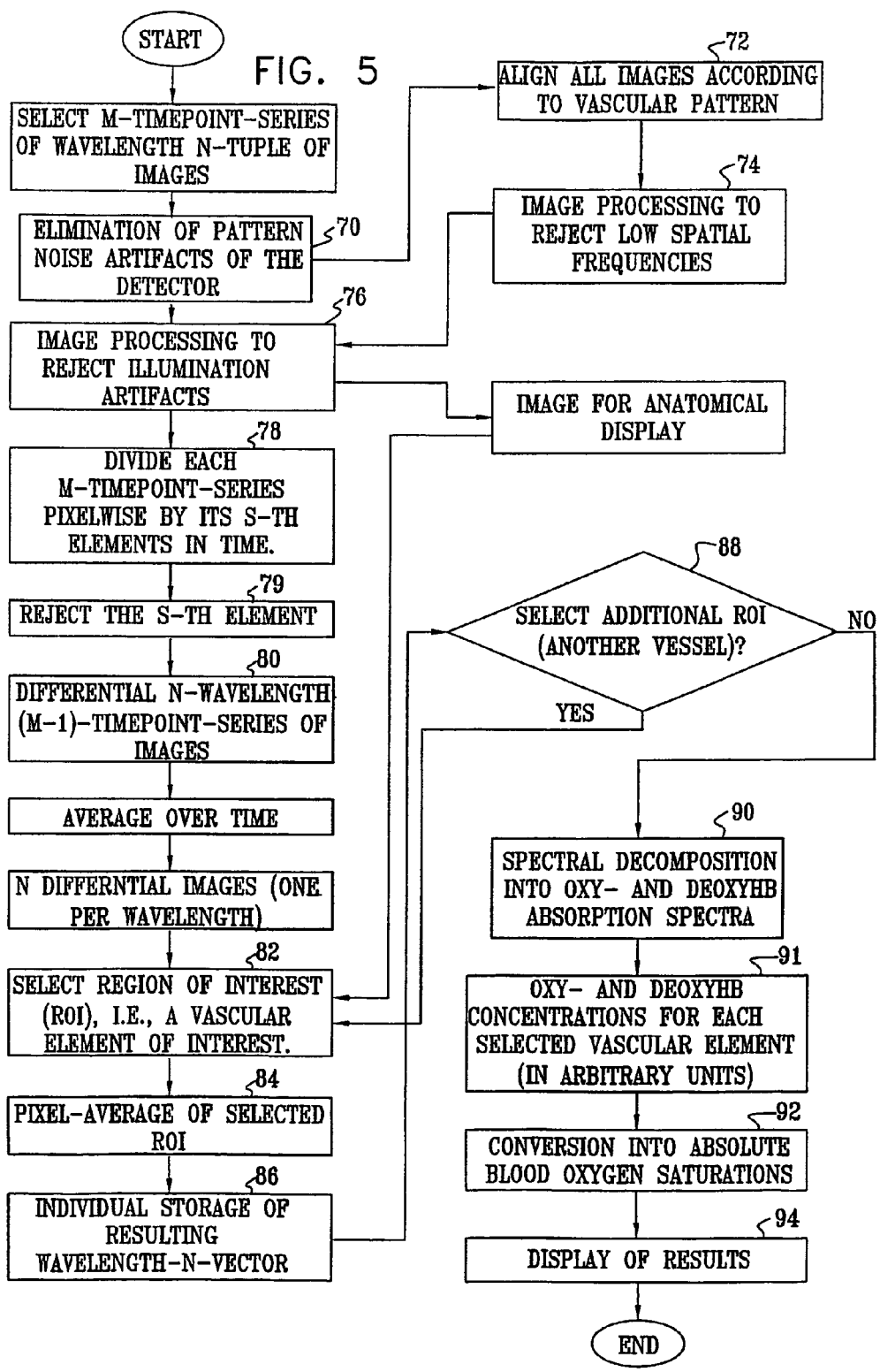

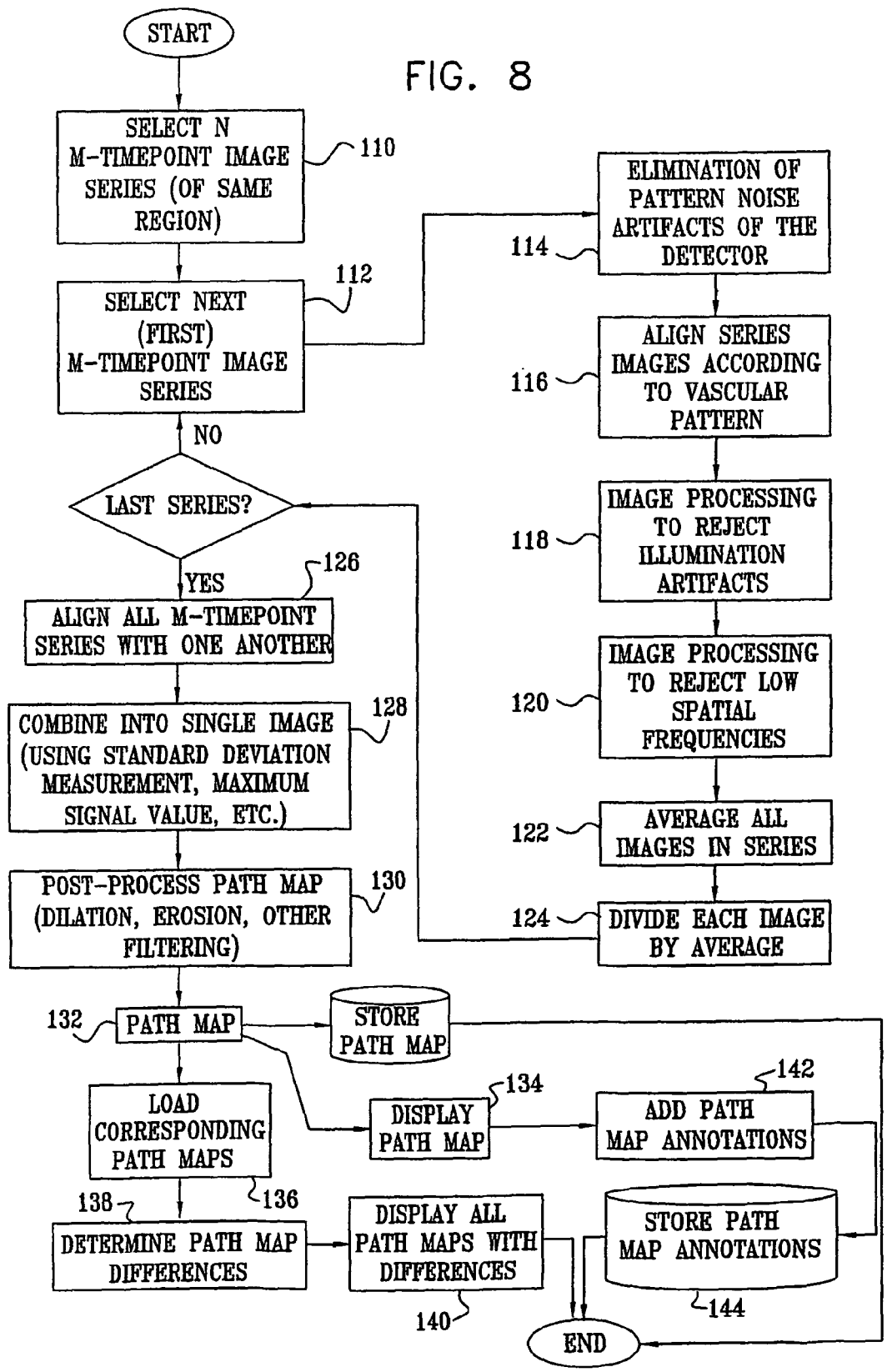

CHARACTERIZATION OF MOVING OBJECTS IN A STATIONARY BACKGROUND

CROSS-REFERENCES TO RELATED APPLICATIONS

This application is a continuation of international application no. PCT/IL03/00275 filed Apr. 2, 2003 which claims the priority of U.S. Provisional patent application Ser. No. 60/369,658 filed Apr. 2, 2002.

FIELD OF THE INVENTION

The present invention relates to the field of detecting chromophores attached to moving objects in a generally stationary spectral background, by separating the known distinct spectra of the moving objects from the overall background spectra, especially as applied to the non-invasive measurement of oxygen saturation in blood vessels by spectrally decomposing the separated spectrum of the moving red blood cells even in blood vessels which do not show significant pulsation, and to the characterization of the paths of blood flow.

BACKGROUND OF THE INVENTION

There are many applications, industrial, scientific and medical, in which it is necessary to determine the quantitative levels of particular components or details of a moving system, wherein the component or detail to be measured is situated in a background environment which may be visually difficult to differentiate from the component or detail to be measured. In such cases, conventional imaging methods are not always adequate.

One such example is in the determination of the oxygen level in the blood supply to a living tissue, or of any other recognizable component of the blood supply. Adequate oxygen supply by the blood to the tissue is a fundamental prerequisite for its correct function. Oxygen supply, however, is often impaired as a result of several acute and/or chronic diseases, such as those involving local changes in blood vessels caused by mechanical obstruction or inflammatory processes. Such changes can result, for instance, as an outcome of arteriosclerosis or diabetes, which can cause damage to the tissue at the systemic level and/or can cause well defined pathologies in specific organs, including the heart, brain, eyes, and others. In particular, diseases involving or resulting from decreased oxygen supply by the retinal vasculature, are one of the leading causes of blindness worldwide. Many of these diseases are both progressive and treatable. Thus, early detection is highly desirable because it may lead to preventive treatment.

In the eye, for example, diagnoses are often made on the basis of structural changes that occur in the retina as a consequence of, or together with problems with the retinal oxygen supply. Such structural changes include the consequences of ischemic events, sometimes necessitating the performance of fluorescent angiographies in order for them to be detected, neovascularization, which is the growth of new blood vessels in an attempt to compensate for a reduction in oxygen supply from pre-existing vessels, cotton-wool patches, which are regions in which nerve fiber axoplasmic transport has failed, and even the degeneration of retinal nerve fibers. Once observed, these and other phenomena may be used to diagnose retinal vascular disease, and to begin treatment to ameliorate further degeneration. But these structural changes are indicative of significant irreversible damage which has already occurred. It is therefore, clearly desirable to detect disease earlier, before structural damage occurs. In many cases, parts of the retina that are suffering damage have an impaired oxygen supply or metabolism, and thus might be capable of identification by local abnormalities in the oxygen saturation of capillary blood. Similarly, properly functioning or particularly active retinal regions could be identified by the local oxygen saturation characteristics of their capillary blood. Together, such information about damaged and intact retinal areas could provide important landmarks for limiting as much as possible the damage to healthy tissue resulting from targeted retinal treatments. This information can be divided into two categories: that pertaining to the blood oxygen saturation level in blood vessels, this requiring a knowledge of the spectral composition of the components of the blood flow; and that pertaining to structural changes in the blood vessel geometry itself whether due to the generation of new blood vessels, such as in neovascularization, or due to the apparent disappearance of blood vessels due to blockage of the flow therethrough. Each of these categories will now be dealt with successively.

Methods for measuring blood oxygen saturation should be rapid, quantitative, objective, and as non-invasive as possible. A number of methods exist in the prior art:

Blood gas analysis provides a method of measuring oxygen saturation in blood with high accuracy. It is, however, invasive, since it requires a blood sample from the point of interest and thus, in many cases, cannot be used. Also, the measurement takes time and cannot be performed continuously. In addition, only arterial or venous oxygenation can generally be measured, or, by making a small cut in the tissue under examination, the oxygenation of a mixture of arteriolar, venular and capillary blood.

Pulse oximetry, on the other hand, is non-invasive, and allows continuous measurement. Pulse oximetry exploits the pulsatile nature of blood supply due to the heartbeat. This introduces heart-rate correlated changes in the concentration of hemoglobin in the perfused tissue. These changes in the concentration in turn cause heart-rate correlated changes in light absorption of the tissue, as opposed to the more constant background absorption of the surrounding tissue. Pulse oximetry, however, cannot be applied to blood vessels or blood vessel irrigated areas where, due to the viscous properties of the blood and the elastic properties of the blood vessel system the heartbeat signal has decayed below the detectability threshold. This occurs in capillaries and post-capillary vessels, and in a large part of the retinal vasculature in general. Thus, pulse oximetry, since it relies on arterial pulsation, can generally be used only to provide information on the oxygenation of arterial blood, and not for other vascular components, and in particular, not for capillaries, venules or small diameter veins.

Many methods for the assessment of the oxygenation of a blood sample rely on spectral analysis, exploiting the different absorption spectra of oxy-hemoglobin ($HbO_2$) and deoxy-hemoglobin (Hbr). Each spectrum is distinct, and therefore, in theory, spectral measurements of a sample in a cuvette at only a few wavelengths can, subject to some assumptions, provide information about the amount of each chromophore. Oxygen saturation, in turn, is related to the ratio of oxy-hemoglobin to deoxy-hemoglobin. The value of oxygen saturation, $SO_2$, can be calculated from the equation $SO_2 = [HbO_2]/\{[HbO_2]+[Hbr]\}$.

In vivo measurements, on the other hand, are more difficult. The main difficulty with in vivo spectrometry methods is posed by the presence of pigments other than oxy- and deoxy-hemoglobin. In the spectral range of interest, the absorption spectra of those pigments, along with those of oxy- and deoxy-hemoglobin, are far from flat, and the portion of the overall spectra due to such pigments is not readily determined in vivo. Furthermore, in spectral measurements relying on reflected light, light intensity is affected not only by chromophores but also by other reflecting entities. Thus, a spectral decomposition of the absolute reflection spectrum is often highly problematic, especially, for instance, in a location such as the retina, where many pigments are involved. Furthermore, reflections from the retina may originate from many sources, and the spectral content of the reflected light is thus affected by chromophores or pigments throughout the surrounding tissue, and not only locally.

Another common disadvantage of all of the above techniques for in vivo oxygen saturation measurement is their intrinsically low spatial resolution, generally allowing the assessment only of systemic blood oxygenation values. None of these techniques allows in vivo visualization of the oxygen saturation in distinct vessels, in particular not at the level of the capillary network and not in a comparative way across the different vascular compartments. Since oxygenation may be different in different capillaries, or as a function of time or of manipulations of the physiological activity, important diagnostic information may be obtained by the use of data sets having image character rather than discrete point-like measurements.

In the present example of retinal diseases, the importance of a more direct method of measuring retinal blood oxygenation is evident from the current interest in fields such as the therapeutic effects of hyperoxia in the case of retinal detachment, described in a publication by R. A. Linsenmeier and L. Padnick-Silver entitled "Metabolic dependence of photoreceptors on the choroids in the normal and detached retina" in Investigative Ophthalmology and Visual Science, Vol. 41(10), pp. 3117-3123 (September 2000), and in the retinal hypoxia characteristic of the early stage of diabetes, before clinically evident retinopathy appears, as described in a publication entitled "Retinal Hypoxia in long-term diabetic cats" by R. A. Linsenmeier et al. published in Investigative Ophthalmology and Visual Science, Vol. 39(9), pp. 1647-1657 (August 1998), and as illustrated by the efforts invested in developing such techniques. A method describing direct oxygen tension measurements performed with a retinal oximeter is published in Diabetes Technol. Ther. Vol. 2(1), pp. 111-3 (Spring 2000). Those measurements were, however, confined to large vessels next to the optical disk in a swine animal model.

There is thus a need for a new method that can measure blood oxygen saturation quantitatively, and which overcomes the presence of other absorbing chromophores or reflecting objects in the tissue. There is also a need for methods that are not single point measurements but offer high resolution images of the values of oxygen saturation and other related parameters in the entire imaged tissue rather than at one point. Such images should preferably be obtained from all vascular types, including capillaries, venules and veins.

In some types of chronic progressive disease involving the vasculature, the decision to begin treatment is directly predicated on the onset of structural changes, which appear to mark a critical point in the disease's progress. Neovascularization in the eye is a structural change that indicates the development of an ocular disease state, which carries a high risk of causing permanent and irreversible damage to the eyesight of a patient Numerous factors are predisposing to neovascularization, prominently including diabetic retinopathy, age-related macular degeneration (AMD) and retinal vascular occlusion. These factors indicate that a patient should be monitored closely for further signs of disease, but by themselves are not enough to begin treatments which themselves may have serious consequences for an individual's sight. Thus, sensitive early detection of the onset of neovascularization is desirable for patients known to be at risk.

Ocular neovascular disease is associated with, and thought to be in part caused by, a deficit in oxygen transport to a region of tissue. Other proposed mechanisms of neovascularization do not necessarily pass through a stage of oxygen deficit. Causes that increase the concentration of angiogenesis factors (such as certain tumors), or that decrease the concentration of vasoinhibitory factors (such as vitrectomy or lensectomy) in the eye may also lead to an increased risk of neovascular disease.

Once begun, neovascularization may progress until it itself becomes a cause of further ocular degeneration through one or more of several mechanisms. By blocking fluid outflow through the trabecular meshwork, neovascularization can contribute directly to the tissue-damaging rise in intra-ocular pressure associated with neovascular glaucoma New vessels are weaker than normal vessels, and prone to hemorrhages that can block sight and reduce blood supply. Hemorrhaging may in turn promote retinal detachment, that leads directly to loss of sight Thus, neovascularization occupies a critical point in the progression of retinal disease, as is more fully described in "Textbook of Glaucoma", by M. Bruce Shields, M.D., published by Lippincott Williams and Wilkins (Philadelphia), 1997.

Not only is it central to the overall disease process, but neovascular disease is also, as mentioned above, treatable. Currently, the most common intervention in the case of a patient who has developed neovascularization of the eye is panretinal photocoagulation (PRP). This technique, though it usually saves the long-term vision of the patient, is partially destructive to existing visual acuity, and is attended by the risk of complications. It is of benefit, therefore, to apply this treatment only in patients where the risk of further disease progression is highest.

For example, PRP treatment of patients with non-proliferative diabetic retinopathy (NPDR) provides measurable, but moderate long-term protective benefit compared to treating patients whose NPDR has already progressed into the more dangerous proliferative diabetic retinopathy (PDR). At the same time, early PRP treatment exposes a number of patients to disadvantage and risk, even though they would not in fact have developed PDR. Refining clinicians' ability to decide which patients should or should not be treated with PRP would thus be of major practical benefit.

By definition, it is the onset of neovascularization that marks the dividing line between NPDR and PDR—the "proliferative" these two terms contain refers to the proliferation of new blood vessels in the eye. Thus, a better method of detecting and measuring neovascularization would serve to aid clinicians in determining which populations of patients should be treated quickly, and those whose diabetic retinopathy is stable, and does not require immediate intervention. A similar argument applies to the treatment of neovascular disease due to other causes, and in other organs besides the eye, such as vascular occlusion, AMD, and tumor-stimulated neovascularization.

Two primary techniques are currently used to diagnose neovascularization in the eye, flourescein angiography and slit lamp examination. Neovascularization of the eye is often noted first in the iris, though it may be seen also in the retina at the same time. The most sensitive of the two examination techniques, fluorescein angiography, detects peripupillary or retinal leakage from newly grown vessels; however, it is an invasive technique that carries a risk of complications. Furthermore, it is often not available to the primary care physicians on whom many patients at risk rely. When neovascularization is sufficiently progressed, slitlamp examination can also directly visualize abnormal new blood vessel growth. However, this visualization is not as sensitive as fluorescein angiography, and again, requires a physician trained to evaluate the findings.

Neovascularization thus occupies a key role in ophthalmic and other diseases, such as cancer, and in governing decisions about treating such diseases. Existing techniques for evaluating neovascularization suffer from the drawbacks of invasiveness, or of insensitivity, and require specially trained medical personnel and/or hospital facilities. There is a need, therefore, for a means of detecting neovascularization which is non-invasive, sensitive, simple to operate, and gives results which may be easily interpreted by the clinician.

Any system or method for the detection of neovascularization by detecting the generation of new blood vessels, should also be useful for the detection of the blockage of existing blood vessels, by the apparent disappearance of such vessels in successive imaging sessions. Such a phenomenon can result as a side-effect of increased intra-ocular pressure, or as a result of sickle-cell anemia.

The disclosures of all publications mentioned in this specification, are hereby incorporated by reference, each in its entirety.

SUMMARY OF THE INVENTION

The present invention provides a system and method for identifying, mapping and characterizing moving objects located within a complex stationary environment and having an optical spectrum which can be distinguished from that of the stationary environment, the stationary environment being also generally unchanging spectrally. According to one preferred embodiment of the present invention, there is provided a system for determining the blood oxygen saturation of blood within tissue, by means of spectral analysis that determines the ratios of oxy- and deoxy-hemoglobin present, even in the presence of other chromophores in the tissue besides the oxy- and deoxy-hemoglobin to be measured. The system is capable of separating the spectra of these two blood-related chromophores, from other chromophores and/or reflecting entities in the tissue outside the microcirculation. The method of measurement used in the system is based on the fact that the blood-related chromophores move with the blood flow along the blood vessels and all their compartments, and thus change their location in space, whereas the chromophores outside the microcirculation are stationary. This movement is independent of the pulsation, such that the system can be used for blood analysis at any point in the microcirculation. The spectrum of the blood-related moving chromophores is thus temporally different from the overall spectrum, and in particular, from the spectra of the stationary chromophores or reflecting entities. Separation of the spectra of moving objects from that of stationary objects is performed by analyzing the spectra as a function of time.

A second preferred aspect of this invention is related to the imaging of the parameters in an entire area, rather than individual point measurements. If the system has an optical resolution capable of resolving single erythrocytes or conglomerates thereof, then from the changes in spatial patterns, time-dependent and time-independent information can be identified and separated by directly comparing at least two images of the tissue taken at different instants of time. For example, by simple subtraction of the two images, the spectral information of moving chromophores is retained whereas the spectra of stationary chromophores and stationary reflecting entities are eliminated.

By acquiring a time series of images at several wavelengths, and by eliminating the contribution of the stationary spectra as described above, the spectra of the moving objects only is obtained. These spectra are then decomposed into the absorption spectra of oxy- and deoxy-hemoglobin, thus allowing assessment of the oxygenation of the blood, independently of the absorption due to the stationary pigments in the image.

As described above, the outlined method preferably comprises two distinct steps: (i) isolation of the spectra of blood related chromophores, primarily oxy- and deoxy-hemoglobin in red blood cells moving within the microvascular system, from the overall spectra that include the contribution of several stationary pigments, and (ii) the spectral decomposition analysis into oxy- and deoxy-hemoglobin absorption spectra.

There is therefore provided, in accordance with a preferred embodiment of the present invention, a system for directly analyzing blood oxygen saturation in blood vessels. The blood flow, preferably in retinal blood vessels, is determined by detecting spatial changes in erythrocyte patterns in images produced of the retina, generally by reflection from the retina The retinal blood flow is preferably measured by tracking individual red blood cells or conglomerates thereof in individual blood vessels in the retina In this manner, individual red blood cells (RBC's) or aggregates thereof, are tracked during their displacements along the blood vessels. In order to do this, pulses of preferably blue and/or green light are flashed in rapid succession into the eye at precisely known intervals, preferably of less than 1 sec., and more preferably within the range of 5-200 ms, so as to permit construction of a "movie" of the movements of the RBC's, or of their aggregates, in the retina. Differences in the retinal reflectance due to differences in the spatial distribution of RBC's in the retina at different instants in time, the "differential image" are then preferably measured. Such a differential image is preferably obtained, in the simplest method of processing the information, by pixel-by-pixel subtraction of two images obtained at different time points. Once the spectral images of the moving chromophores, oxy- and deoxy-hemoglobin, have been isolated from the spectral images of the other chromophores, a spectral decomposition is then preferably performed for the assessment of the hemoglobin oxygen saturation. This whole process is done by acquiring such differential images at several wavelengths, yielding a differential spectrum, which is then spectrally decomposed with the help of a spectroscopic model preferably comprising the absorption spectra of oxy-hemoglobin, deoxy-hemoglobin and a constant term. The recording wavelengths are preferably within the range of the two characteristic oxy- and deoxy hemoglobin derivative absorption peaks (520-590 nm), but can be any other wavelength in the UV/VIS/IR range where difference spectra for these two chromophores exists.

In the case of the retinal example, it is also important that the conditions throughout the wavelength range, under which the images of the retina are taken, remain unchanged, in particular the focal distance of the crystalline lens, and the optical viewing axis. To ensure this, the wavelength dependent images should be acquired either simultaneously or in rapid succession. Rapid wavelength switching can be obtained in several ways. The different wavelengths are sampled, preferably using a computer-driven fast filter wheel, or any other fast wavelength switching or splitting devices. The filter wheel is introduced into the optical path, and quickly switches between optical filters. A filter wheel generally enables the sampling of at least 4 different wavelengths. More filter wheels or other wavelength switching devices can be used in tandem, thus enabling measurements at any number of wavelengths, as needed to obtain detailed spectra necessary to decompose the spectra to the spectrum of the individual oxy and deoxy hemoglobin components. The switching of the wavelength can be performed either on the illuminating light, preferably in the path between the flash source and the imaging optics, or on the light reflected from the retina, preferably in the path between the imaging optics and the detector. In general, wavelength switching or filtering devices have a finite passband, and not a discrete single wavelength line, and throughout this disclosure, and as claimed, use of the term wavelength is understood to include such a finite passband of wavelengths centered at the so-called, desired imaging wavelength.

A preferable and alternative method of rapidly switching the wavelength is by simultaneous detection of the same images at multiple wavelengths after splitting the retinal image into several images, and then selecting the proper wavelength of each image separately. Splitting the image can preferably be accomplished by using prisms, semi-silvered mirrors, split imaging light guides, or similar components. Selection of the wavelength is preferably accomplished by using color filters, interference filters and/or dichroic mirrors.

Alternatively and preferably, a fast tuned spectrometer can be used either to select the desired wavelength of the incident illumination, or to spectrally select the desired wavelength components of the light reflected from the retina.

Small movements of the retinal images during these brief time intervals can preferably be corrected by offline re-registration of the images based on distinct landmarks, particularly the blood vessels themselves, or by aligning areas with correlated reflectance levels, or by other methods known in the art of image processing.

It is a broad object of the present invention to provide a system and a method for directly and non-invasively measuring blood oxygen saturation levels in a tissue that contains other chromophores or reflecting objects. This is achieved by detecting changes in reflectance of individual vascular compartments identified as sub-regions of an image of the region of interest.

In accordance with the present invention, there is therefore provided a system for directly imaging and analyzing blood oxygen saturation in blood vessels, comprising imaging means for acquiring, at predetermined time intervals, at least one pair of images for a plurality of wavelengths, for producing at least one differential image for each wavelength, which, taken together, contain spectral information about moving objects only, that can be translated into information about the level of blood oxygenation.

According to further preferred embodiments of the present invention, the system directly images and analyzes the oxygen saturation in blood vessels, resolving different vascular compartments for their specific blood oxygenation level. Furthermore, the system enables the selective translation of spectral information about moving objects into information about blood oxygenation level in the aforementioned blood vessels.

Whereas the determination of oxygen saturation in the retina has been used in this specification to illustrate one preferred embodiment of the present invention, it is clear to those of skill in the art that the invention can also be used for direct in-vivo detection of oxygen saturation, or of any other gases, in other body organs, by visualizing them appropriately, such as during endoscopy or laparoscopy or similar procedures. Such organs include, but are not limited to, the brain, lungs, heart, liver, kidneys, and the skin. The saturation of other gases in the blood requires appropriate use of their known spectra.

In addition to the above-described preferred embodiments for blood related spectral quantification, another preferred application of the apparatus and methods of the present invention is in the determination of the flow of cerebral spinal fluid (CSF), which poses a biomedical problem in several pathological situations. By labeling the CSF with micro-spheres having well-defined spectral characteristics, the system and methods of the present invention can be used, according to more preferred embodiments, to precisely measure the CSF flow, despite the background color of its immediate environment.

The invention is not necessarily limited to in-vivo measurements Assessments of tissue vitality can also be beneficial in-vitro, outside of the living body, for example, in organs that are prepared for transplantation and whose suitability therefor must be assessed. In such situations, the present invention can be applied beneficially as soon as artificial perfusion of the organ is activated.

There are several other problems that can be solved in-vitro using the system and methods of the present invention. For example, bacteria or parasites often have certain spectrally distinct properties, and furthermore can even be specifically labeled by extrinsic probes or by genetic manipulation labeling, for example with GFP or similar probes. Since bacteria are generally in motion, the system of the present invention can be used for in-vitro blood tests, in-vitro urine tests, and similar biomedical applications, for determining bacterial presence and quantification.

By the incorporation of additional inventive steps, the system and method summarized above using the motion signal for determining spectral characterization of blood vessels in tissue, can also be used for determining path characterization of such vessels. Just as multiple superimposed chromophores contribute to the reflectance of a tissue, so do multiple superimposed structures. In the retina, for example, blood vessels, the structure of interest, are commingled with fascicles of axons and numerous local pigment variations, making the small vessels and capillaries difficult to resolve. So, just as it is useful, for spectral analysis, to find some means of extracting the reflectance of a chromophore of interest from its background; it is useful, for anatomic analysis, to isolate the reflectance due to a structure of interest from its background.

In the case of vascular structures, the reflectance signal due to the motion of red blood cells through the circulation provides a means for performing such isolation. A region that changes its reflectance over a series of images, due to the motion of blood cells, clearly contains a functioning blood vessel near the imaged surface. By combining images, a representation of the imaged surface may be built up, such that every point through which a blood cell cluster passes is marked as being located on a blood vessel. With increasing numbers of images, points that are located on blood vessels link together to reveal segments of vessels, and finally a complete map of the vascular pattern in the region of interest.

This in itself would be of only slight use if the paths along which blood cells move were always clearly visible in single images, like a network of highways seen from the air in the daytime. However, in the case of capillaries and small blood vessels, the path itself is often obscured, due to surrounding structures, or even invisible, due to its own transparency. The capillaries are like unlit back roads at night, only made visible by tracing the path of headlights moving along them.

The earliest vessels formed during vascular neogenesis are themselves capillaries, or structures similar to capillaries— thin walled and invisible, except by means of the blood that passes through them. They are, therefore, targets well suited to visualization through motion signal analysis. Comparisons among vascular patterns imaged over time, or even identification of vascular features unique to neovascularizing tissue, thus provides a means for improved diagnosis of neovascular ophthalmic disease. However, it is to be understood by one of skill in the art that neovascular ophthalmic disease is only meant to be one preferred embodiment of the application of this aspect of the present invention, and the invention is understood to be equally applicable to the detection of other pathological states involving capillary vascular structural changes in tissue, whether involving the detection of the generation of new vascular structures, or the disappearance of existing vascular structures, the latter being applicable for the improved diagnosis of diseases related to the blocking of capillaries.

The system and method for path characterization differs somewhat from the above described system and method for spectral characterization. The isolation of blood-related chromophores, step (i) in the above-described system, is essential to the neovascularization measurement. The spectral decomposition analysis, step (ii) in the above-described system, is however, not an essential step. Thus, using the extended version of the instrument; measurement of blood flow is made as already described, but using images preferably confined to one wavelength range, preferentially a range that combines high hemoglobin absorption with high overall retinal reflection. Nevertheless, the combining of sets of images taken at different wavelengths is also possible, allowing complete reuse of a spectral image data set for the extraction of improved information about vascular anatomy.

Detection of neovascularization thus proceeds initially from a blood-motion image dataset similar or identical to that obtained with the spectral characterization device, including alignment within each image series, differential analysis, and then mutual alignment of the differential images obtained from each series to be included in the analysis. After this point, the operations of the two systems differ.

In order to create the motion path map, the computing and control system 22 must be capable of first determining which regions of the imaged area contain moving chromophores, and which do not Several preferred instantiations of this means are possible. Two illustrative examples, not intended to be limiting, are by measurement of the standard deviation of the reflectance value measured at a point over time, followed by thresholding, and measurement of the maximum difference from the mean value of the point over time, followed by thresholding.

Alternatively and preferably, image processing functionalities may also be provided for linking together nearby points at which motion is measured, such as binary dilation, and/or for removing isolated points which are unrelated to any flow path, such as binary erosion.

The resulting set of points marked to be included or not included on paths are then preferably collected together in a spatially ordered array or map. This map may be treated as an image for display, and means of display are preferably provided, with further provision made for an operator to interactively view and annotate the image according to any finding that can be deduced from a single path map.

Furthermore, the computing and control system is preferably constructed to digitally store the path map and its annotations, so that it can be recalled for comparison with path maps obtained from the same subject and region at a later time.

When more than one path map exists for the same subject and region, the computing and control system is preferably constructed to enable interaction with all corresponding maps together, and in particular for displaying differences among them with emphasis, so that the operator can easily discern both the disappearance of paths along which motion was previously detected, and the appearance of new paths.

Preferably, the system is able to interactively annotate the set of path maps, together with the ability to store them in memory ant to recall them when required.

Advantageously, means are also preferably provided for making morphological measurements on individual paths, including but not limited to parameters such as length, width, and curvature, so as to characterize them, for comparison with subsequent measurements, and also as a means of immediately identifying paths which conform to the characteristics of normal, or of recently formed paths.

Several industrial applications can also benefit from use of this invention, such as in the field of machine vision and artificial intelligence algorithms for inspection of products or complex objects, where moving objects exhibiting spectrally distinct spectra are embedded in an environment that is stationary. Another example is in the field of the quality control of food, in cases where the quality is correlated with distinct spectra that change, and hence move as a function of time.

There is therefore provided, in accordance with one preferred embodiment of the present invention, a method for analyzing material moving in an essentially stationary and unchanging spectral background, comprising the steps of:
  (i) producing at predetermined intervals of time, at least two images at a first wavelength of the moving material in the background,
  (ii) comparing at least among each other, images obtained from at least one set of at least two of the at least two images for determining regions of the images having a changed intensity level at the first wavelength over at least one of the predetermined intervals of time,
  (iii) performing steps (i) and (ii) at at least a second wavelength,
  (iv) performing spectral analysis on the regions of the images having a changed intensity level determined at the first and at the at least a second wavelength, and
  (v) determining from the spectral analysis the quantitative level of chromophores in the moving material.

Step (ii) of this method, and of other methods described in a similar manner in this application, is understood to account for all the preferable methods mentioned in this application of comparing images of moving material in its background, whether performed by comparing single images with single images, or by comparing single images with averages of pluralities of images, or any of the other image comparison methods mentioned herein. Furthermore, in the above mentioned method, the essentially stationary and unchanging spectral background may need to be obtained by post-processing alignment of slightly different images. Additionally, the material may be blood, and the essentially stationary and unchanging spectral background the tissue of a subject, and the chromophores may then be components of the blood.

In accordance with yet another preferred embodiment of the present invention, there is also provided a method for analyzing blood within the tissue of a subject, comprising the steps of:
  (i) producing at predetermined intervals of time, at least two images of the tissue of the subject at a first wavelength,
  (ii) comparing at least among each other, images obtained from at least one set of at least two of the at least two images for determining regions of the images having a changed intensity level at the first wavelength over at least one of the predetermined intervals of time,
(iii) performing the step of producing at second predetermined intervals of time, at least two images of the tissue of the subject at at least a second wavelength,
(iv) comparing at least among each other, images obtained from at least one set of at least two of the at least two images for determining regions of the images having a changed intensity level at the first wavelength over at least one of the predetermined intervals of time,
(v) performing the step of comparing at least among each other, images obtained from at least one set of at least two of the at least two images produced at the at least a second wavelength, for determining regions of the images having a changed intensity level at the at least a second wavelength over at least one of the second predetermined intervals of time, and
(vi) spectrally analyzing the regions having changed intensity levels determined at the first and at the at least a second wavelength to determine concentrations of components of the blood having different spectral characteristics.

In the above described method, the components of blood preferably pertain to the oxygen saturation of the blood, and even more preferably comprise at least one of oxy-hemoglobin and deoxy-hemoglobin Furthermore, the step of spectrally analyzing may be performed by means of signal amplitude analysis, which could preferably be a statistical least squares analysis method.

In accordance with yet more preferred embodiments of the present invention, the tissue may be retinal tissue, in which case the procedure is non-invasive, or optically accessible tissue of an internal organ, such as esophageal, intestinal or brain tissue, which will generally require invasive or semi-invasive procedures.

In accordance with still another preferred embodiment of the present invention, there is provided a method for characterizing material movement in an essentially stationary and unchanging spectral background, comprising the steps of:
(i) producing at predetermined intervals of time, at least two images of the material in the background at a predetermined wavelength,
(ii) comparing at least among each other, images obtained from at least one set of at least two of the at least two images for determining regions of the images having a changed intensity level over at least one of the predetermined intervals of time,
(iii) superimposing the regions of the images in order to generate at least one path map of the material, and
(iv) comparing the at least one path map with a previously obtained path map to determine changes in paths present in the background.

In this method, the material may be blood and the essentially stationary and unchanging spectral background a tissue of a subject, and the path maps are then maps of vascular paths present in that tissue. Furthermore, the changes may be either the appearance of new vascular paths or the disappearance of previously present vascular paths.

In accordance with yet more preferred embodiments of the present invention, the tissue may be retinal tissue, in which case the procedure is non-invasive, or optically accessible tissue of an internal organ, such as esophageal, intestinal or brain tissue, or the internal surface of a passageway, which will generally require invasive or semi-invasive procedures. Furthermore, in the above mentioned methods, the essentially stationary and unchanging spectral background may need to be obtained by post-processing alignment of slightly different images.

There is further provided in accordance with still another preferred embodiment of the present invention, a method for characterizing material movement in an essentially stationary and unchanging spectral background, comprising the steps of:
(i) producing at predetermined intervals of time, at least two images of the material in the background at a predetermined wavelength,
(ii) comparing at least among each other, images obtained from at least one set of at least two of the at least two images for determining regions of the images having a changed intensity level over at least one of the predetermined intervals of time,
(iii) superimposing the regions of the images in order to generate at least one path map of the material, and
(iv) inspecting the at least one path map to determine the characteristics of paths present in the background.

In the above method, the material may be blood and the essentially stationary and unchanging spectral background tissue of a subject, and the paths are then vascular paths present in that tissue. The characteristics determined may be abnormalities in vascular morphology. Furthermore, the tissue may be retinal tissue, in which case the procedure is non-invasive, or optically accessible tissue of an internal organ, such as esophageal, intestinal or brain tissue, or the internal surface of a passageway, which will generally require invasive or semi-invasive procedures. Also, in the above mentioned methods, the essentially stationary and unchanging spectral background may need to be obtained by post-processing alignment of slightly different images.

In accordance with a further preferred embodiment of the present invention, there is also provided a system for analyzing material moving in an essentially stationary and unchanging spectral background, comprising: a light source for illuminating the material in the background,
a wavelength selector for defining at least a first and a second wavelength,
an imager for acquiring at predetermined intervals of time at least two images at the at least first and second wavelengths of the material in the background,
a discriminator comparing at least among each other, images obtained from at least one set of at least two of the at least two images, at each of at least two of the wavelengths, and determining regions of changed intensity level,
a spectral analyzer adapted to determine the spectra of the regions of changed intensity level determined by the discriminator, and
a chromophore level calculator, utilizing the output of the spectral analyzer to determine the quantitative level of chromophores in the moving material.

The above-described system may also comprise a post-processing image aligner adapted to align images obtained from slightly misaligned regions of the essentially stationary and unchanging spectral background. Furthermore, the material may be blood and the essentially stationary and unchanging spectral background the tissue of a subject, and the chromophores are then components of the blood. Furthermore, the tissue may be retinal tissue, in which case the procedure is non-invasive, or optically accessible tissue of an internal organ, such as esophageal, intestinal or brain tissue, or the internal surface of a passageway. Additionally, the chromophores may preferably be components of blood pertaining to oxygen saturation, and the chromophore level calculator is an oxygen blood level determiner.

In any of the above-described systems, the wavelength selector may be located in the illuminating pathway between the light source and the material in the background, or in the imaging pathway between the material in the background and the imager, or in the imager itself. The wavelength selector is preferably a computer controlled filter wheel, and the light source, preferably a computer controlled flash lamp.

There is further provided in accordance with yet another preferred embodiment of the present invention, a system for analyzing tissue of a subject, comprising:

(i) a light source for illuminating the tissue,
(ii) an imager for acquiring at predetermined intervals of time, at least two images of the tissue,
(iv) a discriminator comparing at least among each other, images obtained from at least one set of at least two of the at least two images, and determining regions of changed intensity level, and
(v) a superpositioner for generating at least one map of vascular path positions from the regions of changed intensity level.

The system may also preferably comprise a path map comparator using the at least one map of vascular path positions and a previously obtained vascular path map, to determine changes in vascular paths present in the tissue of the subject. Alternatively and preferably, it may comprise an output display device for showing the at least one vascular path map to determine the characteristics of vascular paths present in the tissue of the subject. The light source is preferably a computer controlled flash lamp, and the system also preferably comprises a wavelength selector defining an imaging wavelength range.

There is even further provided in accordance with a preferred embodiment of the present invention, a system for characterizing material movement in an essentially stationary and unchanging spectral background comprising:

(i) a light source for illuminating the material and its background,
(ii) an imager for acquiring at predetermined intervals of time, at least two images of the material and its background,
(iv) a discriminator comparing at least among each other, images obtained from at least one set of at least two of the at least two images, and determining regions of changed intensity level, and
(v) a superpositioner for generating at least one path map of the material from the regions of changed intensity level.

The above-described system preferably also comprises a path map comparator using the at least one path map of the material and a previously obtained path map, to determine changes in paths present It also preferably comprises an output display device for showing the at least one path map to determine the characteristics of paths of the material and a wavelength selector defining an imaging wavelength range.

BRIEF DESCRIPTION OF THE DRAWINGS

The present invention will be understood and appreciated more fully from the following detailed description, taken in conjunction with the drawings in which:

FIG. 1A is a schematic diagram illustrating a system for determining the oxygen saturation in the blood vessels of living organs, according to a preferred embodiment of the present invention.

FIGS. 2A to 2C are a series of schematic drawings showing representations of how the spatial pattern of an erythrocyte changes in time with motion of the erythrocyte down a blood vessel, and how the motion information can be separated from the static information;

FIG. 5 is a schematic flowchart illustrating the steps taken, according to a preferred method of the present invention, for analyzing the data obtained by the steps of the flowchart of FIG. 4, and for determining the blood oxygen saturation levels for each area of interest in the imaged area;

FIG. 8 is a flowchart illustrating the steps taken, according to another preferred method of operation of the system of FIG. 6D of the present invention, for analyzing the data obtained by the methods of the flowchart of FIG. 7, and for determining a complete path map for an area of interest in the imaged area.

DETAILED DESCRIPTION OF PREFERRED EMBODIMENTS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented to provide what is believed to be the most useful and readily understood description of the principles, conceptual aspects and relevant details of the invention. The description, taken with the drawings, should make it apparent to those skilled in the art how the several forms of the invention may be embodied in practice.

Reference is now made to FIG. 1A which is a schematic block diagram illustrating a system, constructed and operative according to a preferred embodiment of the present invention, for determining the oxygen saturation in the blood vessels of living organs. In FIG. 1A, the system is shown performing the measurements non-invasively on the blood vessels in a retina, but it is to be understood that the system is equally useful for application to the blood vessels in other organs, as described hereinabove, such as by using an endoscopic or laparoscopic probe for illuminating and imaging the surface tissues of optically accessible internal organs, such as the esophagus or the surface tissue of the brain.

Figure 1B:
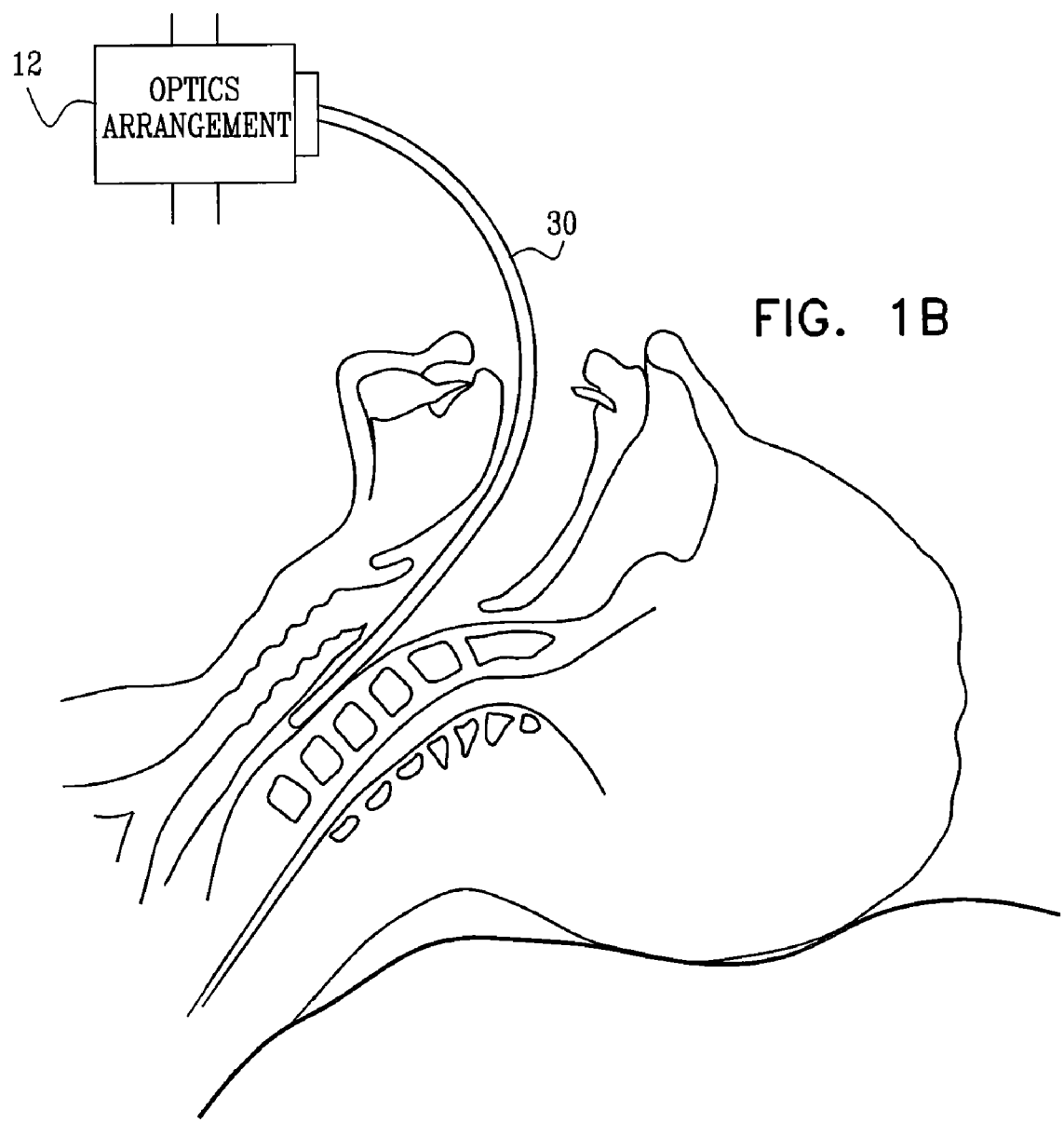
FIG. 1B is an insert drawing showing a preferred embodiment of the imaging optics arrangement of FIG. 1A, including a fiber optical probe in use for imaging the surface of a generally inaccessible organ of a subject.

The system 10 of FIG. 1A comprises an imaging optics arrangement 12, for imaging the surface layers of the organ of interest For imaging the retina 16, the imaging optics arrangement 12, is preferably a fundus camera or an ophthalmoscope. For imaging other internal organs, the imaging optics arrangement can preferably include a high quality objective head, or a macro-camera lens, and can preferably include an optical endoscopic or laparoscopic probe for imaging organs generally inaccessible from outside the body. Such an arrangement is shown schematically in FIG. 1B which shows a preferred imaging optics arrangement including a fiber optical probe 30 in use for imaging the surface of a subject's esophagus, as an example of the inspection of a generally inaccessible internal organ Likewise, the system 10 can also be used, according to further preferred embodiments of the present invention, for the analysis of the flow in paths other than blood vessels in the tissues of a subject, by the use, inter alia, of suitably adapted imaging optics and data processing modules.

The imaging optics arrangement 12 preferably contains a beam splitting device, a mirror with a central transmission aperture, or other optical arrangement, such that the input illumination, in the presently described embodiment, coming from a flash lamp 14, though any other suitable illuminating source may also preferably be used, can be directed towards the illuminated organ tissue 16, along the same optical path as the image information obtained by reflection or scatter from the illuminated tissue of interest 16. The imaging information is preferably received by a high resolution imaging device, such as a CCD camera 18. The output image data from this camera 18 is preferably input to a image acquisition device 20, such as a digital frame grabber, whose output data is processed by a computing and control system 22, which also controls the timing of the preferred flash lamp 14. The computing and control system 22 preferably comprises a multiple imager and processor 22a, a discriminator 22b for image sequence comparison, and a spectral analyzer 22c, which preferably incorporates an oxygen blood level determiner, utilizing the data output of the spectral analyzer. After generation of the output data, they are preferably directed to a display monitor 24 and/or a printer 26. The operation of each of the component modules of the computing and control system 22 will be more fully explained hereinbelow with reference to the flow charts of FIGS. 4A, 4B and 5. The system may also preferably include a component arrangement for calibrating the illuminating flash, both for spatial variations and for overall intensity variations, as for instance described in the PCT patent application published as International Publication Number WO 99/63882 for "Imaging and Analyzing Movement of Individual Erythrocytes in Blood Vessels" to A. Grinvald and D. Nelson, hereby incorporated by reference in its entirety. Such an arrangement is only necessary if the uniformity of the illuminating source is insufficient, or if the intensity varies significantly from flash to flash.

A wavelength selecting device 28, 28a is added to the illuminating beam path or the imaged beam path such that narrow bands of incident illumination are used for sequentially imaging the blood vessels in the retina at different preselected wavelengths. Alternatively and preferably, the spectral selection can be performed using facilities enabled within the imaging system or camera itself, such as a multiple detector array 28b, each array detecting a particular wavelength band. The typically used bandwidth is 2 to 30 nm These wavelength-selecting elements differ from the bandpass filters mentioned in the system described in the abovementioned publication WO 99/63882, where a filter is required in order to provide a bandwidth of light which improves the contrast of the image of the erythrocytes. Since the erythrocytes absorb strongly in the blue and green areas of the spectrum, the filter is required in that prior art system in order to improve their contrast with the relatively reflective retina against which they are imaged, and which also contains a large number of pigments of differing colors. In the present invention, on the other hand, the wavelength selector is necessary to perform the extraction of the separate spectral contributions of the oxy- and deoxy-hemoglobin components of the blood at wavelengths that are preselected to be at peaks of the difference spectra between oxy- and deoxy-hemoglobin, and at the isosbestic wavelength, at which the absorption of the two chromophores happen to be identical, which is used as a control wavelength for the employed spectroscopic model used in analyzing the data.

Spectrally resolved images of essentially the same region should be acquired virtually simultaneously but at different wavelengths. This is preferably accomplished by use of a computer-driven fast filter wheel as the wavelength selection device 28, 28a. However, any other fast, controllable color switching or splitting device can also be used, as explained hereinabove, with the control commands to change the wavelength selection coming from the computing and control system 22.

Reference is now made to FIGS. 2A to 2C, which are a series of schematic drawings showing representations of how the spatial pattern of an erytirocyte changes in time with motion of the erythrocyte down a blood vessel, and methods of separating the motion information from the static information. Due to the blood flow, clusters of erythrocytes, as shown in FIGS. 2A and 2B as black dots, move down a blood vessel segment, depicted in FIGS. 2A and 2B as the white trace. As a result, different spatial erythrocyte patterns are seen in the same blood vessel segment at different times.

FIG. 2A schematically shows the erythrocyte distribution in the blood vessel segment at time $t_A$. FIG. 2B shows the erythrocyte distribution in the same blood vessel segment at a time $t_B$, which is later than $t_A$, typically by an interval of from a few milliseconds to a hundred milliseconds or more, depending on the blood vessel being observed. The spatial erythrocyte patterns in FIG. 2B have changed compared to FIG. 2A. The crosshair in FIGS. 2A and 2B denotes the same spatial location on the vessel. FIG. 2C shows the resulting image when the two images of FIGS. 2A and 2B are subtracted, one from the other. The difference image obtained thus shows up the changes in reflection due to the movement of the erythrocytes. Black and white circle patterns result, due to the displacement of the erythrocytes in FIG. 2A as compared to FIG. 2B. FIG. 2C is an enlarged view of the small rectangle seen on the center of the crosshairs in FIGS. 2A and 2B. Since the location of the blood vessel itself (white) and the background tissue (gray) is unchanged between the two images, these structures cancel out upon subtraction, leaving only information pertinent to the moving erythrocytes. The above procedure is known from the above-mentioned PCT International Publication Number WO 99/63882. This information, in the form of images of the moving erythrocytes, is then preferably stored in the memory modules of the computing and control system 22, for comparison and processing in the stages to be described below.

Using the system of FIG. 1A of the present invention, this procedure is now preferably repeated several times at different wavelengths. The wavelength-dependent information obtained from the moving objects only is then processed, preferably by the computing and control; system 22, to enable the spectra of the moving erythrocytes to be decomposed into the absorption spectra of the chromophores contained in the erythrocytes, in this case oxy- and deoxy-hemoglobin.

Figures 3A, 3B:
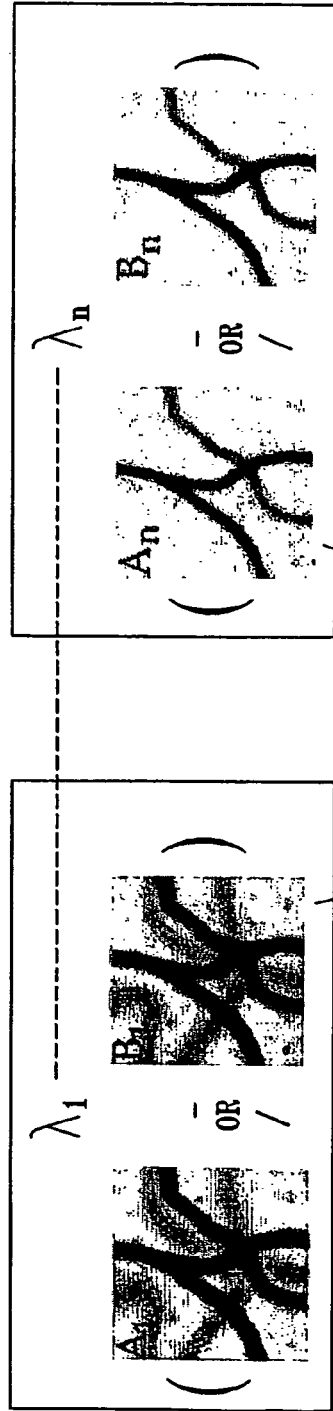
FIGS. 3A to 3D are a sequence of schematic drawings showing images of the retinal vasculature for different wavelengths, to illustrate a preferred method of extracting spectral information about the moving objects only, in this case the erythrocytes.

Reference is now made to FIGS. 3A to 3D, which are a sequence of schematic drawings showing images of the retinal vasculature, illustrating how spectral information is obtained about the moving objects only, in this case the erythrocytes. In FIGS. 3A and 3B, the figures in the top row marked $A_1$ and $B_1$ are two images obtained at a wavelength of $\lambda_1$ in a sequence rapid enough that the stationary information in the images can be regarded as being truly stationary. Although for illustrative purposes, only two images are depicted, a series of several images, typically 6-8 or more, are preferably acquired at each wavelength, in order to increase the quantity and hence the reliability of the data obtained at each wavelength. The same procedure is then repeated at several wavelengths $\lambda_1$ to $\lambda_n$. As is observed from the differences between the pair of images marked $A_1$ and $B_1$ and those marked $A_n$ and $B_n$, the contrast of the vasculature obtained at different wavelengths is different.

Figure 3C:
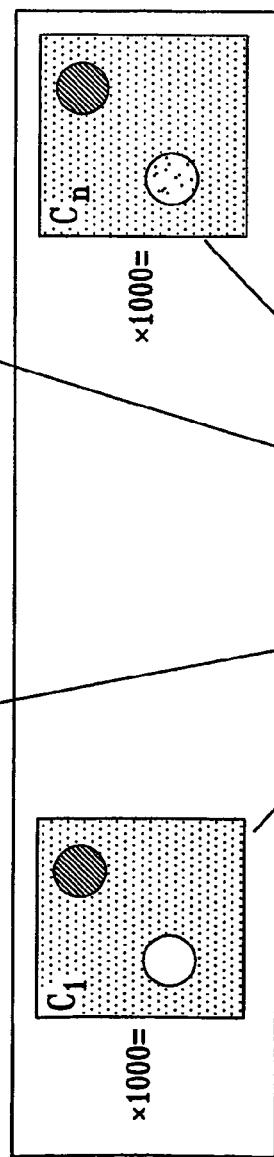

Reference is now made to FIG. 3C, in which FIG. $3C_1$ is a differential image, obtained by subtracting images $A_1$ and $B_1$, in the manner described in FIGS. 2A to 2C. Similarly, differential images are generated for each wavelength, up to $\lambda_n$ where the differential image marked $C_n$ is obtained. More preferably, the differential images are obtained by dividing images $A_1$ and $B_1$, this procedure being operative to correct for uneven illumination. Even more preferably, the differential images are obtained by dividing each individual frame $A_1$ by an averaged frame $B_1$ obtained from the 6-8 closely timed images mentioned above. When the differences in illumination are small, the subtraction procedure and the division procedure are essentially equivalent. In the examples shown in FIGS. 3A and 3B, since the difference between each pair of images is very small compared to the images themselves, the results have been enhanced by multiplying the differential images in FIG. 3C by a constant factor, in the case shown, by a factor of 1000.

According to an alternative preferred embodiment, the measurements are performed on the system by generating FIGS. $3A_1$ to $3A_n$ as a series of images obtained in relatively rapid sequence at several wavelengths $\lambda_1$ to $\lambda_n$, preferably as simultaneously as possible. This is accomplished by means of the high speed switchable filter, 28 or 28a, as shown in the system of FIG. 1A. FIGS. $3B_1$ to $3B_n$ are a series of images of the same retinal vasculature as in FIGS. $A_1$ to $A_n$, obtained at the same wavelengths $\lambda_1$ to $\lambda_n$, in rapid sequence by use of the high speed switchable filters, or, more preferably, obtained essentially simultaneously, but at a time later than the time during which the series of images $A_1$ to $A_n$ was acquired. The images $B_1$ to $B_n$ are taken, however, close enough to those of $A_1$ to $A_n$ to warrant that the stationary information in the images can be regarded as being truly stationary, after alignment has been performed on the images. Again, according to this alternative preferred embodiment, although for illustrative purposes only two series of images ($A_i$ and $B_i$) are depicted, a series of 6-8 images are preferably acquired. FIGS. $3C_i$ to $3C_n$ are a series of differential images, obtained by subtracting or dividing images $A_i$ and $B_i$.

Figure 3D:
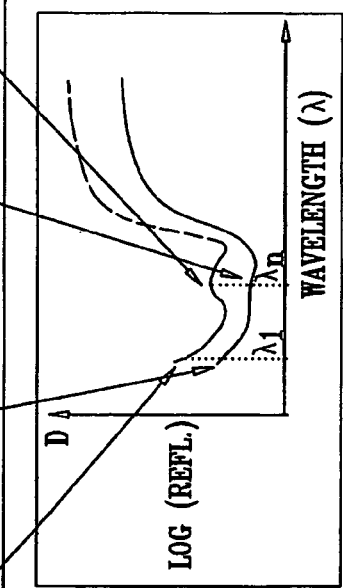

Reference is now made to FIG. 3D, which is a series of graphs of the reflection spectra obtained from the raw images of FIGS. $3A_1$ to $3A_n$ and FIGS. $3B_1$ to $3B_n$ and from the differential images of FIGS. $3C_1$ to $3C_n$ obtained at the selected different wavelengths. The solid curve in FIG. 3D is obtained from the images of FIGS. $3A_1$ to $3A_n$ though it could have been obtained from FIGS. $3B_1$ to $3B_n$ instead, and shows a typical reflection spectrum obtained from the series of images containing both time-dependent and stationary spectral information. These two components come respectively from the spectral properties of the blood and the spectral properties of the background tissues, such as the walls of the blood vessels, the surrounding tissue, pigments other than hemoglobin, etc. If this spectrum were to be decomposed into the spectra of the chromophores known to be contained in the moving objects only, namely the erythrocytes, and the levels of oxy- and deoxy-hemoglobin thuswise calculated, the result would yield incorrect values for the respective concentrations, because of the unknown spectral contribution of the stationary elements of the image. The dashed curve in FIG. 3D, on the other hand, shows a typical reflection spectrum obtained from those parts of the differential images containing only time-dependent spectral information, i.e. information about the hemoglobin oxygenation in the erythrocytes within the imaged vessels. This spectrum can thus be correctly decomposed into oxy- and deoxy-hemoglobin, yielding the correct values of their respective concentrations.

The spectral decomposition is preferably performed by use of a linear spectroscopic model of the Beer-Lambert type (unmodified or modified to include wavelength-dependence of path length), and a minimum least square fit of the model equations to the experimental data, comprising the oxy- and deoxy-hemoglobin concentrations as free parameters and preferably, a term encoding light scattering contributions. Images are preferably acquired at at least three wavelengths. These wavelengths are preferably within the range of the characteristic hemoglobin absorption peaks (520-590 nm) and are preferably chosen so as to provide at least three independent equations for solving the equations resulting from the preferred spectroscopic model used. In the general case, the number of chromophores with unknown concentration appearing in the particular spectroscopic model sets the lower limit for the number of independent equations required, and thus determines the minimum number of wavelengths at which to acquire images. Additional wavelengths, however, can be added irrespective of the particular spectroscopic model, either as a control for the validity of the model or to tune model parameters which otherwise have to be deduced from theoretical considerations, or to increase the signal to noise of the spectral decomposition algorithm (preferably minimum squares fit).

The differential spectra shown in FIG. 3D are preferably recorded for many sub-regions of the image, and even down to each pixel, yielding an oxygen saturation map of the entire imaged area This procedure enables the identification of, and the differentiation between healthy and pathological regions of the imaged area.

Figure 4A:
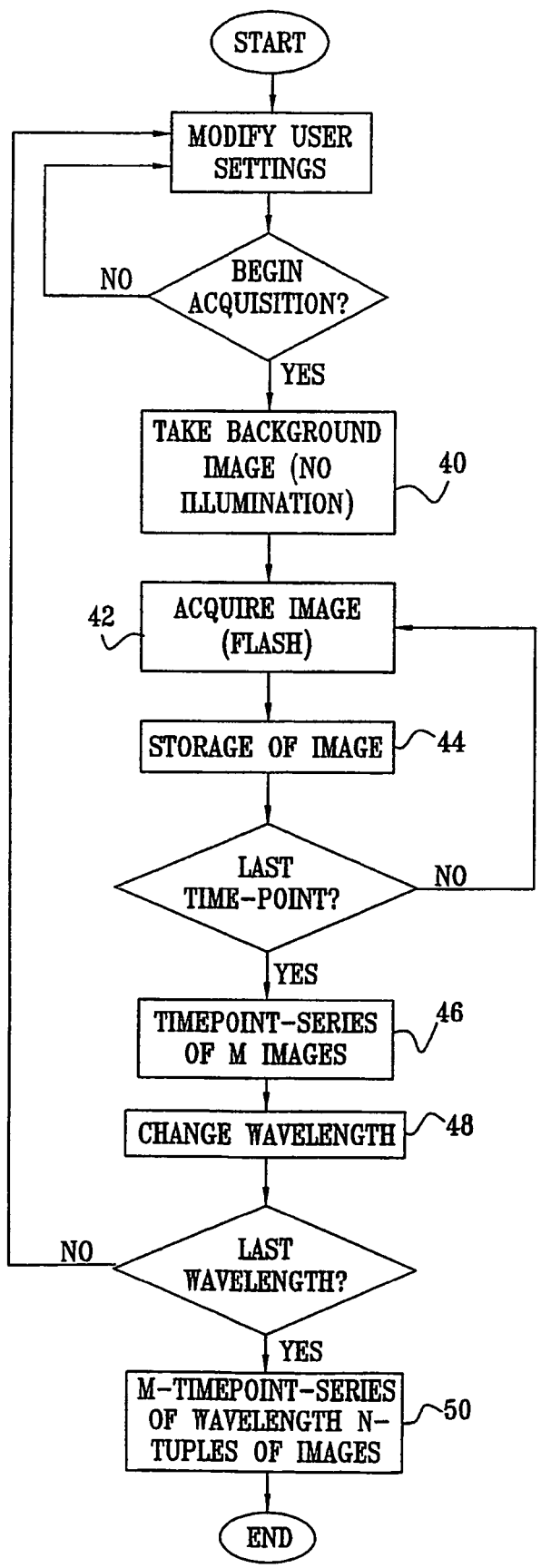
FIGS. 4A and 4B are schematic flowcharts illustrating the steps taken in the system of FIG. 1A, for acquiring the spectral image data of the area of interest to be analyzed.

Reference is now made to the flowchart of FIG. 4A, which illustrates the steps taken, according to a preferred method of operation of the system of FIG. 1A of the present invention, for acquiring the spectral image data of the area of interest Step 40. Background image taken (no illumination).

Step 42. Flash in order to take image of the area of interest.

Step 44. Storage of image.

Step 46. Fast repetition of steps 44 to 46 at intervals of 15-40 millisecond, k times, k being the number of flashes required to get a clear motion signal, and preferably approximately 6 to 8 flashes.

Step 48. Wavelength change (e.g. filter wheel advances one step).

Step 50. Repetition of steps 40 to 46 n times, where n=3, to obtain a "wavelength n-tuple" of images at the same focus.

Figure 4B:
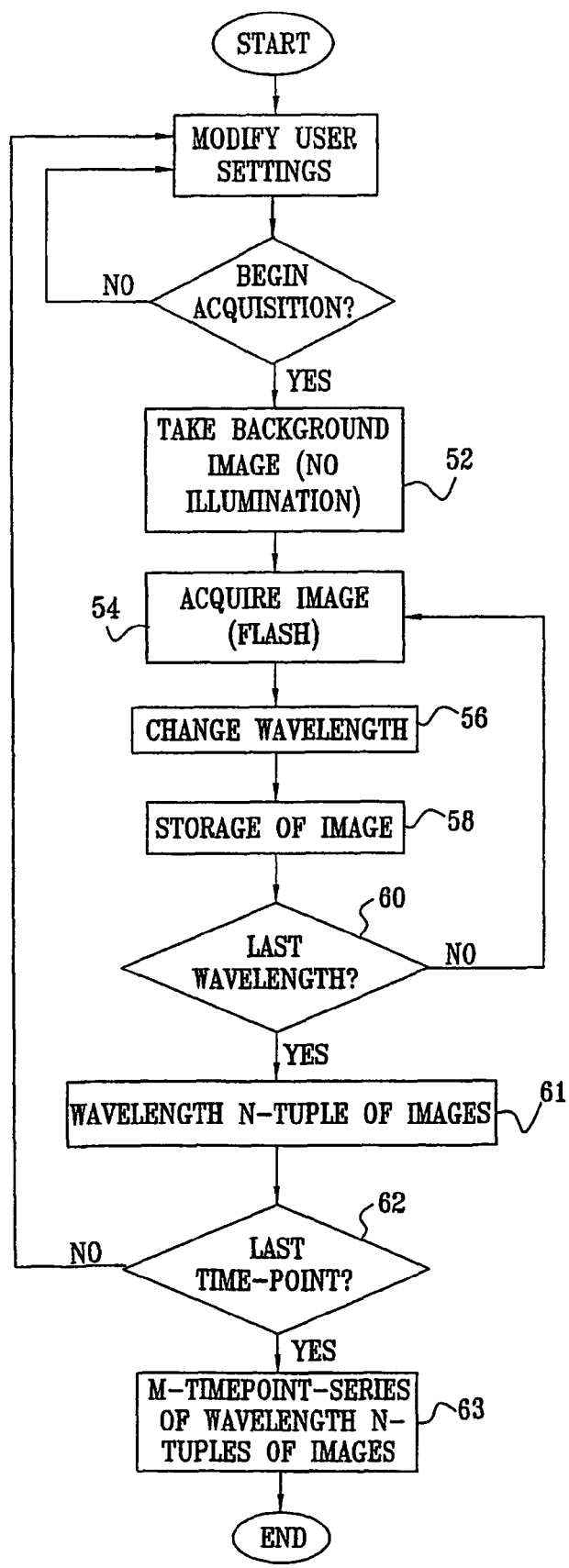

Alternatively and preferably, a modified sequence of steps can be used for acquiring the spectral image data of the area of interest, as illustrated in FIG. 4B. This modified sequence corresponds to the alternative preferred embodiment described above in relationship to FIGS. 3A to 3D, as follows:

Step 52. Background image taken (no illumination).

Step 54. Flash in order to take image of the area of interest.

Step 56. Wavelength change (e.g. filterwheel advances one step).

Step 58. Storage of image.

Steps 60-61. Rapid repetition of steps 54 to 58 n times (n being the number of wavelengths used, where n=3) to obtain a "wavelength n-tuple" of images at the same focus.

Steps 62-63. Repetition, each time at a different wavelength, of steps 52 to 60 m times (m=2) to obtain an "m-timepoint-image-series" of wavelength-n-tuples.

Another alternative and preferable embodiment of the method for acquiring the spectral image data of the area of interest, performed in place of step 58 above, is the simultaneous acquisition of each image across all wavelengths of interest, as previously mentioned, preferably using facilities enabled within the imaging system or camera itself, such as multiple detector arrays.

Reference is now made to the flowchart of FIG. 5, which illustrates the steps taken, according to a preferred method of operation of the system of FIG. 1A of the present invention, for analyzing the data obtained by the methods of the flowcharts of FIG. 4A or 4B, and for determining the blood oxygen saturation levels for each area of interest in the imaged area Step 70. Elimination of pattern noise artifacts of the detector, performed on the m-timepoint series of wavelength n-tuples of images obtained at the output of the data acquisition processes shown in FIG. 4A or 4B.

Step 72. Alignment of all images according to the vascular patterns on the retina Step 74. Image processing, preferably high-pass filtering of the images to reject information with spatial frequency significantly lower than that of the retinal vasculature Step 76. Elimination of possible illumination artifacts by image processing.

Steps 78-79. Creation of differential image series; for example, by dividing each wavelength n-tuple pixel-by-pixel-wise by its s-th element (1=s=m) of the m-timepoint-image-series, and rejecting thereafter the s-th element of the resulting m-series.

Step 80. Creation of a "main differential image n-tuple" by averaging the differential wavelength (m'11)-series obtained in steps 78-79 over time (t=1 ... m−1), yielding one image for each wavelength.

Step 82. Manual selection of a "region of interest", i.e. the relevant vascular element from one of the images obtained in step 76, and creating the mathematical intersection of the selected subset of image onto the "main differential image n-tuple", image-by-image-wise ("ROI").

Step 84. Pixel average of the ROI selected in step 82, yielding a "wavelength-vector" with n-elements (one for each wavelength).

Step 86. Storage of the wavelength-vector.

Step 88. Repetition of steps 82 to 86 to select different vascular elements, with separate storage of wavelength-vectors as many times as desired by the user.

Step 90-91. Spectral decomposition of the logarithm of the wavelength-vectors into a linear combination of the extinction coefficient of oxyhemoglobin, deoxyhemoglobin, and a wavelength-independent term, by means of a least mean square fit, for each of the wavelength-vectors selected by the user. This step yields the concentrations of oxy- and deoxyhemoglobin multiplied by the optical path length.

Step 92. Conversion of the concentrations of oxy- and deoxyhemoglobin obtained in step 91 into blood oxygen saturations for each vascular element.

Step 94. Display of results.

It is to be emphasized, though, that the described algorithms in FIGS. 4A to 5 are only one method by which the relevant data is processed and extracted, and that other methods known in the art can equally well be utilized, if they provide the necessary data analysis procedures for determining the blood oxygen saturation levels of the blood flow in the regions of interest.

Figure 6A:
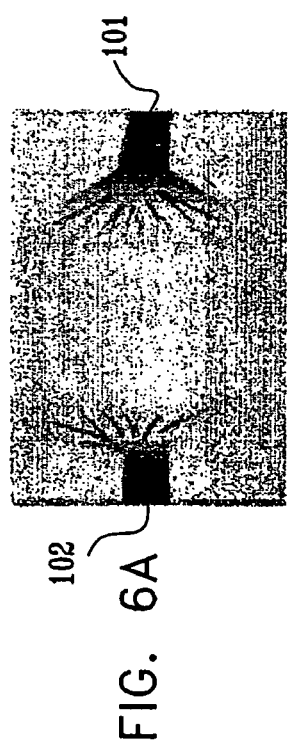
FIGS. 6A to 6C are schematic representations of successive images of an area of tissue where neovascularization or capillary blocking is thought to be taking place, and the path map generated from differential images derived from the individual image frames.
Figure 6B:
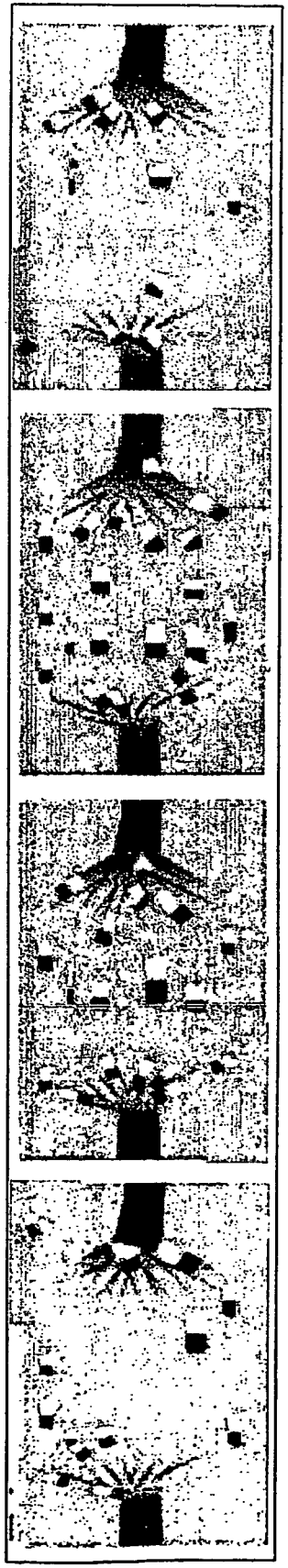
Figure 6C:
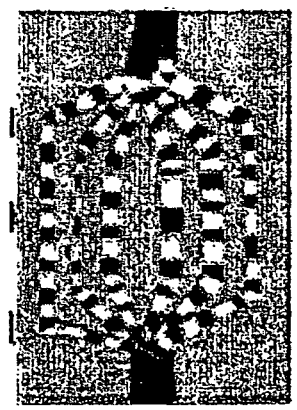
Figure 6D:
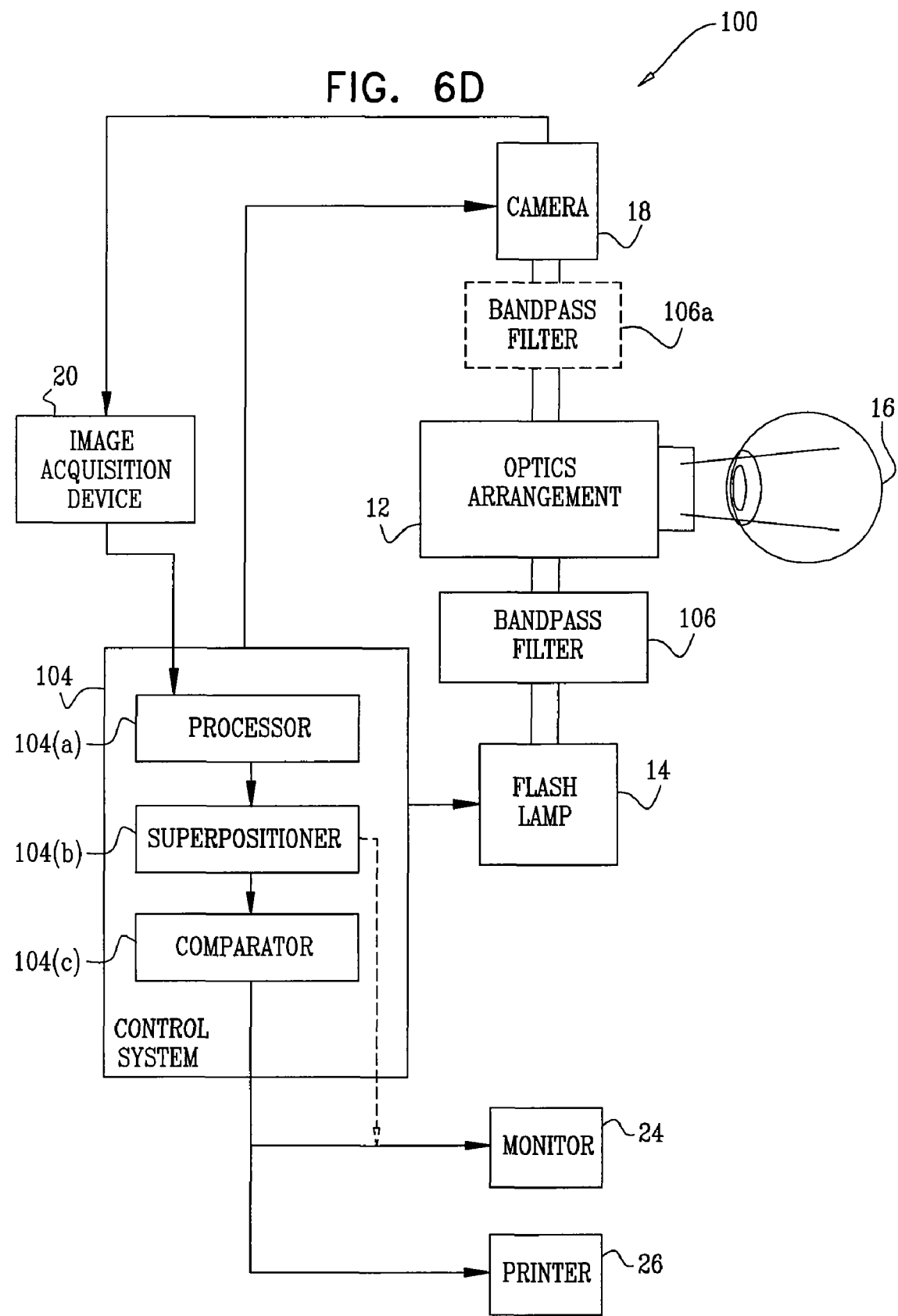
FIG. 6D is a schematic diagram illustrating a system, according to a preferred embodiment of the present invention, for producing images such as those shown in FIGS. 6A to 6C, and for determining therefrom the presence or extent of neovascularization or capillary blocking in the tissue under inspection.

Reference is now made to FIGS. 6A to 6C, which are schematic representations of the successive images produced in an area of tissue where neovascularization or capillary blocking is thought to be taking place, the images being used in order to create a complete motion map of the erythrocytes in the blood vessels present from particle flow information obtained discretely in a sequence of separate images. FIG. 6D is a schematic representation of an imaging system, constructed and operative according to a further preferred embodiment of the present invention, suitable for the determination of the presence of neovasularization or of capillary blocking in the tissues of a subject. The system of FIG. 6D is described more fully hereinbelow.

FIG. 6A is now a schematic diagram of a single-frame image of blood vessels constraining the paths of particle flow within the region of interest, such as can be produced by the apparatus of FIG. 6D, with the wavelength selecting device preferably fixed at a wavelength which provides good contrast between the absorbing hemoglobin in the blood vessels and the reflection from the retinal tissue. The extremities of the two large, visible vessels shown 101, 102, are joined by smaller, mostly invisible vessels in the center of the drawing, though which particles flow in passage between the large vessels. It is apparent that from such a single frame image, little can be learnt about the vasculature between the two large vessels. However, using the system of the present invention, a timed series of images of the area of interest is generated, in a manner similar to that described hereinabove, and the images stored in the memory of the computer and control system for further processing. These digital images of the same regions are then either subtracted from each other to produce a set of sequential differential images, or more preferably, each separate timed image is repeatedly captured in fast succession several times, 6-8 times in the preferred embodiment described herein, by successive flashes of illumination, and the resulting set of preferably 6-8 images averaged, and used as a divisor for each successive separate timed image. The generation of the differential images by these two methods is thus similar to that described hereinabove in relation to FIG. 3.

Reference is now made to FIGS. $6B_1$ to $6B_4$ which show schematic differential images, containing black-and-white spots, representing clusters of dark moving particles or their absence, respectively, and generated by differential analysis of sequential frames as described above. It should be readily apparent that the flow of "gaps" in the sequence of particles flowing through a region are a source of path information, just as the clusters of the particles themselves are. The four separate differential images generated in FIGS. $6B_1$ to $6B_4$ each show randomly different positions of erythrocyte clusters in motion down different capillaries. For reference purposes, the differential images are superimposed on the diagram of the visible vessels 101, 102, so that the relative positions of the erythrocyte clusters within the capillary vessels can be related to the stationary visible vessels.

Reference is now made to FIG. 6C which shows the result of the superposition of the spots visible in the differential images of FIGS. 6B.sub.1 to 6B.sub.4. The spots trace out the paths of the vessels through which the moving particles pass, such that although the vessels themselves are invisible in any single frame, their spatial position can be made apparent as a virtual position by this superposition procedure. Post-processing steps, as described with respect to 130 in FIG. 8, below, may preferably be added to convert this superposition into a final motion map.

The complete motion map, defining the path map of the capillaries in the region of interest, can then be compared with similar maps obtained previously of the same region in the same subject, and stored digitally in the memory of the system. The presence of neovascularization or the disappearance of functioning vessels, can be readily determined either by visual comparison by the system operator, or by the attending clinician, or by algorithmic methods based on known image processing techniques.

Reference is now made to FIG. 6D, which is an outline schematic drawing of a system 100 such as can be used for obtaining the images shown in FIGS. 6A to 6C. The system of FIG. 6D, in a similar manner to that of FIG. 1A, is shown imaging a retinal area 16, though it is to be understood that by use of suitable optical arrangements, any optically accessible tissue can be examined for the purpose of characterizing the vascular structure therein. Likewise, the system 100 can also be used, according to further preferred embodiments of the present invention, for characterizing paths other than blood vessels in the tissues of a subject.

The system 100 comprises an imaging optics arrangement 12, for imaging the surface layers of the organ of interest. For imaging the retina 16, the imaging optics arrangement 12, is preferably a fundus camera or an ophthalmoscope. For imaging other internal organs, the imaging optics arrangement can preferably include a high quality objective head, or a macro-camera lens, or can preferably include an optical endoscopic or laparoscopic probe for imaging organs generally inaccessible from outside the body, such as is shown schematically in FIG. 1B above. The imaging optics arrangement 12 preferably contains a beam splitting device, a mirror with a central transmission aperture, or other optical arrangement, such that the input illumination, shown as coming from a flash lamp 14 in this preferred embodiment, though any other suitable illuminating source may also preferably be used, can be directed towards the illuminated organ tissue 16, along the same optical path as the image information obtained by reflection or scattering from the illuminated tissue of interest 16. A bandpass filter 106, 106a is generally required in order to enable the system to operate within a bandwidth of light which improves the contrast of the image of the erythrocytes against the relatively reflective retina, which also contains a large number of pigments of differing colors. The wavelength filtering device can be inserted in any suitable position in the beam path.

The imaging information is preferably received by a high resolution imaging device, such as a CCD camera 18. The output image data from this camera 18 is preferably input to a image acquisition device 20, such as a digital frame grabber, whose output data is processed by a computing and control system 104, which also controls the timing of the preferred flash lamp 14. The computing and control system 104 preferably comprises a multiple image series acquirer and motion discrimination processor 104a, a differential image superpositioner for generating path maps 104b, and a path map comparator 104c, which may call on previously generated path maps stored in the memory of the computing and control system 104 or elsewhere, and which processes the data for output to a display monitor 24 and/or a printer 26. Alternatively and preferably, the generated path map or maps may be directly output from the path map comparator 104c, to the display device 24, so that the operator or attending physician can inspect the path map itself to ascertain any unusual changes in the morphology of the paths, or in their presence or lack of presence. The operation of each of the component modules of the computing and control system 104 is more fully explained hereinbelow with reference to the flow charts of FIGS. 7 and 8.

Figure 7:
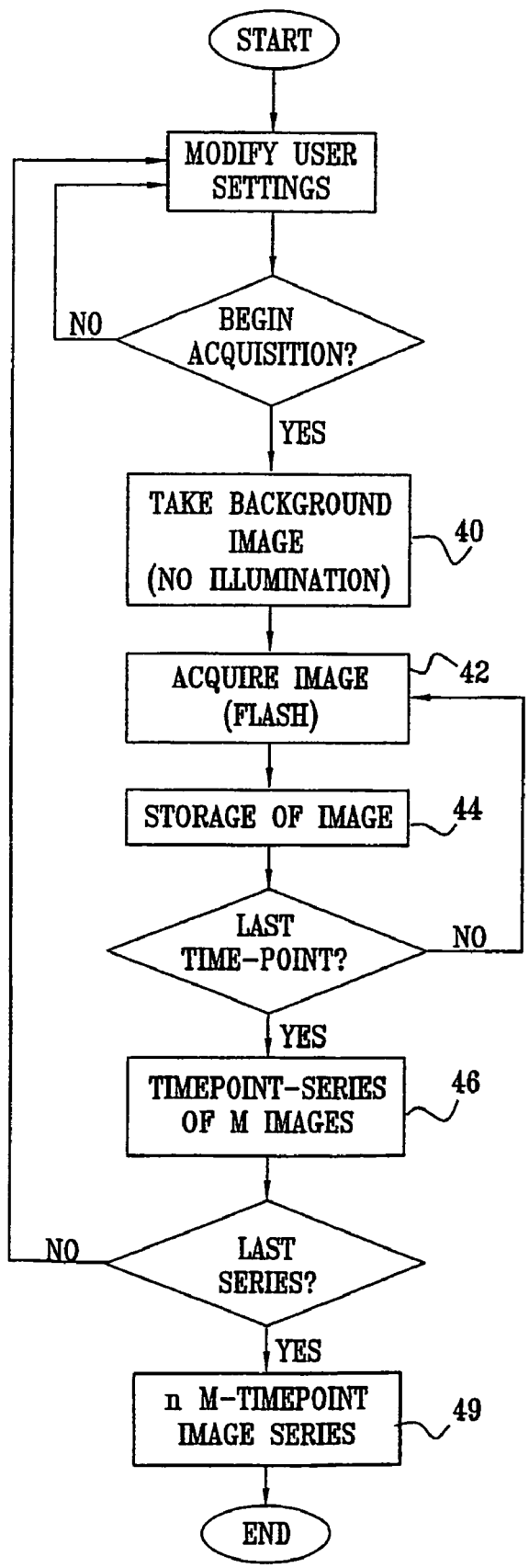
FIG. 7 is a flowchart illustrating the steps taken, according to a preferred method of operation of the system of FIG. 6D of the present invention, for acquiring image data for the determination of a motion map of erythrocyte clusters within an area of interest in a subject.

Reference is now made to the flowchart of FIG. 7, which illustrates the steps taken, according to a preferred method of operation of the system of FIG. 6D of the present invention, for acquiring image data for the determination of a motion map of erythrocyte clusters within an area of interest in a subject The steps are similar to those used in the embodiment of FIG. 4A, with the exception that step 48 of FIG. 4A, involving the changing of the wavelength of the illumination or detection functionality, can be omitted, such that the output of the last step 49 is the generation only of a series of n m-timepoint images.

Reference is now made to the flowchart of FIG. 8, which illustrates the steps taken, according to a preferred method of operation of the system of FIG. 6D of the present invention, for analyzing the data obtained by the methods of the flowchart of FIG. 7, and for determining the complete path map for an area of interest in the imaged area, and for storing and comparing this path map with others obtained at different times on the same subject.

Steps 110 to 126 are essentially similar to steps 70 to 86 of the embodiment shown in FIG. 5, with the exception that the measurements are generally performed at a single wavelength. In step 128, all of the separate differential images accumulated in step 126 are superposed to generate a single image of the area of interest, by one of the methods known in the art such as measurement of the standard deviation of the measured reflectance values followed by thresholding, or measurement of the maximum difference from the mean value of the point over time, followed by thresholding, as mentioned hereinabove.

In step 130, known image processing techniques are used for post-processing the generated path map to produce a smoother resulting map, which is finalized in step 132. In steps 134 to 144, the generated path map is stored in the system memory, displayed on the system monitor 24, annotated if desired by the operator, and other maps taken of the same region of interest of the same subject may preferably be called from memory, for either visual comparison with the map finalized in step 132, or for comparison by means of signal processing algorithms with previously obtained maps. Hard copies of any of these maps can also be optionally printed out on the system printer 26.

It is to be emphasized, though, that the described algorithms in FIGS. 7 and 8 illustrate only one method by which the relevant data is extracted and processed, and that other methods known in the art can equally well be utilized, if they provide the necessary data analysis procedures for determining the path location from motion determination of the blood flow in the regions of interest.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method for performing oximetry on blood of a blood vessel within stationary tissue of a subject, comprising the steps of:
   (i) at separate times, acquiring images at a first wavelength of said blood vessel within said stationary tissue;
   (ii) at separate times, acquiring images at a second wavelength of said blood vessel within said stationary tissue;
   (iii) automatically, eliminating spectral information relating to the stationary tissue by generating respective differential images of said blood vessel within said stationary tissue at said first and second wavelengths, based upon said images acquired at said first and second wavelengths, said images resolving discrete particles within said blood vessel, said particles selected from the group consisting of erythrocytes and aggregates of erythrocytes, even when said blood vessel does not show significant pulsation; and
   (iv) performing oximetry with respect to said discrete particles by:
      (a) performing spectral analysis on each pixel of said differential images, the spectral information relating to the stationary tissue having been eliminated;
      (b) calculating, from said spectral analysis of said differential images, quantitative relative levels of two blood-related chromophores in said particles of said blood vessel; and
      (c) generating an output in response to the quantitative relative levels of the two blood-related chromophores in said particles.

2. The method according to claim 1, wherein acquiring images of said blood vessel within said stationary tissue comprises post-process alignment of slightly different images.

3. A method for performing oximetry on blood of a blood vessel within stationary tissue of a subject, comprising the steps of:
   at separate times, acquiring images of said blood vessel and said tissue of said subject at a first wavelength;
   at separate times, acquiring images of said blood vessel and said tissue of said subject at a second wavelength;
   automatically, eliminating spectral information relating to the stationary tissue by generating respective differential images of said blood vessel within said stationary tissue at said first and second wavelengths, based upon said images acquired at said first and second wavelengths, said images resolving discrete particles within said blood vessel, said particles selected from the group consisting of erythrocytes and aggregates of erythrocytes, even when said blood vessel does not show significant pulsation; and
   performing oximetry with respect to said discrete particles by:
      spectrally analyzing each pixel of said differential images, the spectral information relating to the stationary tissue having been eliminated, to calculate relative concentrations of two blood-related chromophores within said particles of said blood vessel, respective species of chromophores of the blood-related chromophores having different spectral characteristics; and
      generating an output in response to the relative concentrations of the two blood-related chromophores in said particles.

4. A method according to claim 3, wherein calculating relative concentrations of the two blood-related chromophores within said particles of said blood vessel comprises determining oxygen saturation of said blood by determining relative concentrations of oxy-hemoglobin and deoxy-hemoglobin in said blood.

5. A method according to claim 3, wherein said step of spectrally analyzing comprises spectrally analyzing by means of signal amplitude analysis.

6. A method according to claim 5, wherein said step of spectrally analyzing comprises spectrally analyzing by means of a statistical least squares analysis method.

7. A method according to claim 3, wherein said tissue includes retinal tissue, and wherein acquiring images of said blood vessel and said tissue comprises producing images of a blood vessel within said retinal tissue.

8. A method according to claim 3, wherein acquiring images of said blood vessel and said tissue comprises acquiring images of said blood vessel and said tissue non-invasively.

9. A method according to claim 3, wherein said tissue includes optically accessible tissue of an internal organ, and wherein acquiring images of said blood vessel and said tissue comprises acquiring images of a blood vessel within said optically accessible tissue of the internal organ.

10. A method according to claim 9, wherein said tissue includes tissue selected from the group consisting of esophageal, intestinal and brain tissue, and wherein acquiring images of said blood vessel and said tissue comprises acquiring images of a blood vessel within the selected tissue.

11. A system for performing oximetry on blood of a blood vessel within stationary tissue of a subject, comprising:
    a light source for illuminating said blood vessel and said tissue;
    a wavelength selector for defining a first and a second wavelength;
    an imager for (a) acquiring, at separate times, images at said first wavelength of said blood vessel in said tissue, and (b) acquiring, at separate times, images at said second wavelength of said blood vessel in said tissue;
    a discriminator adapted to automatically, eliminate spectral information relating to the stationary tissue by generating respective differential images of said blood vessel within said stationary tissue at said first and second wavelengths, based upon said images acquired at said first and second wavelengths, said images resolving discrete particles within the blood vessel, the particles selected from the group consisting of erythrocytes and aggregates of erythrocytes, even when said blood vessel does not show significant pulsation;
    a spectral analyzer adapted to determine the spectra of said discrete particles, by spectrally analyzing each pixel of the differential images, the spectral information relating to the stationary tissue having been eliminated, and to generate an output in response to said determined spectra; and
    a chromophore level calculator, adapted to perform oximetry on said blood by utilizing the output of said spectral analyzer to calculate quantitative relative levels of two blood-related chromophores in said particles of said blood vessel.

12. A system according to claim 11, and also comprising a post-processing image aligner adapted to align images obtained from slightly misaligned regions of said blood vessel within said stationary tissue.

13. A system according to claim 11, wherein said tissue includes retinal tissue, and wherein said imager comprises an imager selected from the group consisting of: a fundus camera and an ophthalmoscope.

14. A system according to claim 11, wherein said tissue includes optically accessible tissue of an internal organ, and wherein said imager comprises an endoscope.

15. A system according to claim 14, wherein said tissue includes tissue selected from the group consisting of esophageal, intestinal and brain tissue, and wherein said imager comprises an endoscope.

16. A system according to claim 11, wherein said chromophores include oxy-hemoglobin and deoxy-hemoglobin, and said chromophore level calculator is an oxygen blood level determiner.

17. A system according to claim 11, wherein said wavelength selector is a computer controlled filter wheel.

18. A system according to claim 11, wherein said light source is a computer controlled flash lamp.

* * * * *